US009068000B2

(12) United States Patent
Clemmons et al.

(10) Patent No.: US 9,068,000 B2
(45) Date of Patent: Jun. 30, 2015

(54) MONOCLONAL ANTIBODIES FOR ENHANCING OR INHIBITING INSULIN-LIKE GROWTH FACTOR-I

(75) Inventors: David R. Clemmons, Chapel Hill, NC (US); Laura A. Maile, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 477 days.

(21) Appl. No.: 13/474,294

(22) Filed: May 17, 2012

(65) Prior Publication Data

US 2012/0269816 A1 Oct. 25, 2012

Related U.S. Application Data

(63) Continuation of application No. 12/498,719, filed on Jul. 7, 2009, now Pat. No. 8,187,595, which is a continuation-in-part of application No. 11/123,290, filed on May 6, 2005, now Pat. No. 7,723,483.

(60) Provisional application No. 60/657,151, filed on Feb. 28, 2005, provisional application No. 60/569,147, filed on May 7, 2004.

(51) Int. Cl.
| | |
|---|---|
| *A61K 39/395* | (2006.01) |
| *C07K 16/28* | (2006.01) |
| *A61K 39/00* | (2006.01) |

(52) U.S. Cl.
CPC ............ *C07K 16/2848* (2013.01); *A61K 39/00* (2013.01); *A61K 39/3955* (2013.01); *C07K 2317/34* (2013.01)

(58) Field of Classification Search
None
See application file for complete search history.

(56) References Cited

U.S. PATENT DOCUMENTS

| | | |
|---|---|---|
| 5,336,618 A | 8/1994 | Coller |
| 5,578,704 A | 11/1996 | Kim |
| 5,753,230 A | 5/1998 | Brooks |
| 5,965,710 A | 10/1999 | Bodmer et al. |
| 6,369,204 B1 | 4/2002 | Kim et al. |
| 6,531,580 B1 | 3/2003 | Huse et al. |
| 6,590,079 B2 | 7/2003 | Huse et al. |
| 6,596,850 B1 | 7/2003 | Huse |
| 6,887,473 B1 | 5/2005 | Brooks et al. |
| 7,354,586 B2 | 4/2008 | Brooks et al. |
| 7,371,382 B2 | 5/2008 | Huse et al. |
| 7,422,744 B2 | 9/2008 | Huse et al. |
| 7,723,483 B2 | 5/2010 | Clemmons et al. |
| 8,062,635 B2 | 11/2011 | Hattori et al. |
| 8,093,360 B2 | 1/2012 | Casey |
| 8,206,706 B2 | 6/2012 | Clemmons et al. |

| | | |
|---|---|---|
| 2003/0195147 A1 | 10/2003 | Pillutla |
| 2009/0226452 A1 | 9/2009 | Clemmons et al. |
| 2014/0072568 A1 | 3/2014 | Clemmons et al. |

FOREIGN PATENT DOCUMENTS

| | | |
|---|---|---|
| WO | WO 92-07871 A1 | 5/1992 |
| WO | WO 00-55181 A1 | 3/2000 |

OTHER PUBLICATIONS

Speicher et al, Exp Opinion Emerging Drugs, 2003, 8:239-250.*
Wang et al, Diabetes, 1995, 44:161-164.*
Frystyk et al, Diabetic Med, 2003, 20:269-276.*
Feldmann et al, Growth Hormone & IGF Res, 2000, 10:53-59.*
Hellstrom et al, Pediatrics, 2003, 112:1016-1020.*
Grant et al, Expert Opin Invest Drugs, 2004, 13:1275-1293.*
Gura (1997, Science 278:1041-1042).
http://www.chemicon.com/webfiles/PDF/AB1932.pdf (as downloaded on Mar. 19, 2007).
Johnstone and Thorpe (Immunochemistry in Practice, 2$^{nd}$ Ed. 1987, Blackwell Scientific Publications, Oxford, p. 30 and pp. 49-50).
Marions et al, 1998, Molecular Human Reproduction 4(5):491-495.
Tagaki et al. (1997, The Journal of Bioloical Chemistry 272(32):19794-19800).
Higashi et al, "IGF-1, Oxidative Stress, and Atheroprotection" *Trends Endocrinol Metab* 21(4):245-254 (2010).
Catherwood et al. "Glucose-Induced Oxidative Stress in Mesangial Cells" *Kidney International* 61:599-608 (2002).
Cochrane and Robinson, "In Vitro Glycation of Glomerular Basement Membrane Alters its Permeability: a Possible Mechanism in Diabetic Complications" *FEBS Letters* 375:41-44 (1995).
Coppey et al, "ACE Inhibitor or Angiotensin II Receptor Antagonist Attenuates Diabetic Neuropathy in Streptozotocin-Induced Diabetic Rats" *Diabetes* 55:341-348 (2006).
Larsen and Rolin, "Use of the Göttingen Minipig as a Model of Diabetes, with Special Focus on Type 1 Diabetes Research" *ILAR J* 45(3):303-313 (2004).
Marshall et al, "Early Micro- and Macroanglopathy in the Streptozotocin Diabetic Minipig" *Res Exp Med* 177:145-158 (1980).
Tesch and Allen, "Rodent Models of Streptozotocin-Induced Diabetic Nephropathy" *Nephrology* 12:261-266 (2007).
Tuttle and Anderson. "A Novel Potential Therapy for Diabetic Nephropathy and Vascular Complications: Protein Kinase C β Inhibition" *American Journal of Kidney Diseases* 42(3):456-465 (2003).
Gomez et al, (2001) "Acute Pancreatitis Signals Activation of Apoptosis-Assoclated and Survival Genes in Mice" *Exp. Biol. Med.*, 226(7), pp. 692-700.
Hoyne et al. (2000) "Properties of an insulin receptor with an IGF-1 receptor loop exchange in the cysteine-reich region." *FEBS Letter* 469, pp. 57-60.
International Search Report and Written Opinion for International Application No. PCT/US2005/15957 mailed Jun. 19, 2006.
Supplementary Partial European Search Report for EP 05804812.5, Jun. 14, 2007.
Kricker J A et al. Structural and functional evidence for the interaction of insulin-like growth factors (IGFs) and IGF binding proteins with vitronectin. Endocrinology (Jul. 2003), vol. 144, No. 7, pp. 2807-2815.

(Continued)

*Primary Examiner* — Mark Halvorson
(74) *Attorney, Agent, or Firm* — Sterne, Kessler, Goldstein & Fox P.L.L.C.

(57) ABSTRACT

The present invention provides αVβ3 integrin cysteine loop domain agonists and antagonists (including peptide agonists and antagonists and analogs thereof), along with methods of using the same.

7 Claims, No Drawings

(56) References Cited

OTHER PUBLICATIONS

Vogel B E et al, A novel integrin specificity exemplified by binding of the alphaV-beta5 integrin to the basic domain of the HIV tat protein and vitronectin. The Journal of Cell Biology (Apr. 1993), vol. 121, No. 2, pp. 461-468.

Clemmons D R et al. Synthetic alphaVbeta3 antagonists inhibit insulin-like growth factor-I-stimulated smooth muscle cell migration and replication. Endocrinology (1999), vol. 140, No. 10, pp. 4616-4621.

Grulich-Henn J et al. Transport of insulin-like growth factor-I across endothelial cell monolayers and its binding to the subendothelial matrix. Experimental and Clinical Endocrinology and Diabetes (2002), vol. 110, pp. 67-73.

Beer J H et al. Immobilized Arg-Gly-Asp (RGD) peptides of varying lengths as structural probes of the platelet glycoprotein IIb/IIIa receptor. Blood (1992), vol. 79, pp. 117-128.

Coller B S Anti-GPIIb/IIIa Drugs: Current Strategies and Future Directions. Thromb. Haemost. (2001) 86:427-443.

Coller B S Binding of Abciximab to αVβ3 and Activated αMβ2 Receptors: With a Review of Platelet-Leukocyte Interactions. Thromb. Haemost, (1999) 82:326-336.

Gutheil J C et al. Targeted Antiangiogenic Therapy for Cancer Using Vitaxin: A Humanized Monoclonal Antibody to the Integrin αVβ3. Clinical Cancer Research (2000) 6:3056-3061.

Maile L A et al. The Heparin Binding Domain of Vitronectin is the Region that is Required to Enhance Insulin-Like Growth Factor-I Signaling. Mol. Endocrin, (2006) 20(4):881-892.

Maile L A et al. Insulin-Like Growht Factor-I Signaling in Smooth Muscle Cells is Regulated by Ligand Binding to the 177CYDMKTTC184 Sequence of the β3-Subunit of αVβ3, (2006) 20(2):405-413.

Filizola M et al. Mechanistic insights from a refined three-dimensional model of integrin $α_{IIb}β3$. The Journal of Biological Chemistry. 270(23); Jun. 4, 2004: 24624-24630.

Thermo Scientific: Pierce Protein Research Products, Keyhole Limpet Hemocyanin (KLH) activated with SMCC crosslinker for immunogen preparation with cysteine peptides and other sulfhydryl-containing haptens. Product description. 2009. Downloaded May 26, 2009.

Thermo Scientific: Pierce Protein Research Products. Instructions: Imject® Maleimide Activated mcKLH. 2009. Product description. Downloaded May 26, 2009.

Artoni, A. et al. (2004) "Integrin β3 regions controlling binding of murine mAb 7E3: Implications for the mechanism in integrin αIIbβ3 activation" *Proceedings of the National Academy of Science.* 101(36), pp. 13114-13120.

Clemmons, D.R. et al. (2005) "Interaction between Insulin-Like Growth Factor-1 Receptor and αVβ3 Integrin Linked Signaling Pathways: Cellular Responses to Changes in Multiple Signaling Inputs" *Molecular Endocrinology.* 19(1), pp. 1-11.

Xiong, J. et al, (2002) "Crystal Structure of the Extracellular Segment of Integrin αVβ3 in Complex with an Arg-Gly-Asp Ligand" *Science.* 296, pp. 151-155.

Clemmons et al. "Synthetic αVβ3 Antagonists Inhibit Insulin-Like Growth Factor-I-Stimulated Smooth Muscle Cell Migration and Replication" *Endocrinology* 140:4616-4621 (1999).

Imai and Clemmons, "Roles of Phosphatidylinositol 3-Kinase and Mitogen-Activated Protein Kinase Pathways in Stimulation of Vascular Smooth Muscle Cell Migration and Deoxyribonucleic Acid Synthesis by Insulin-Like Growth Factor-I" *Endocrinology* 140:4228-4235 (1999).

Ling et al, "Tyrosine Phosphorylation of the β3-Subunit of the αVβ3 Integrin is Required for Membrane Association of the Tyrosine Phosphatase SHP-2 and its Further Recruitment to the Insulin-Like Growth Factor I Receptor" *Molecular Endocrinology* 17(9):1824-1833 (2003).

Maile and Clemmons. "Integrin-Associated Protein Binding Domain of Thrombospondin-1 Enhances Insulin-Like Growth Factor-I Receptor Signaling in Vascular Smooth Muscle Cells" *Circ Res* 93:925-931 (2003).

Maile and Clemmons, "The αVβ3 Integrin Regulates Insulin-Like Growth Factor I (IGF-I) Receptor Phosphorylation by Altering the Rate of Recruitment of the Src-Homology 2-Containing Phosphotyrosine Phosphatase-2 to the Activated IGF-I Receptor" *Endocrinology* 143:4259-4264 (2002).

Maile and Clemmons, "Regulation of Insulin-Like Growth Factor I Receptor Dephosphorylation by SHPS-1 and the Tyrosine Phosphatase SHP-2" *The Journal of Biological Chemistry* 277(11):8955-8960 (2002).

Maile et al. "Hyperglycemia Alters the Responsiveness of Smooth Muscle Cells in Insulin-Like Growth Factor-I" *Endocrinology* 148(5):2435-2443 (2007).

Maile et al. "Insulin-Like Growth Factor I $α_vβ_3$ Affinity by Increasing the Amount of Integrin-Associated Protein That is Associated With Non-Raft Domains of the Cellular Membrane" *The Journal of Biological Chemistry* 277(3):1800-1805 (2002).

Maile et al, "Modulation of Integrin Antagonist Signaling by Ligand Binding of the Heparin-Binding Domain of Vitronectin to the αVβ3 Integrin" *Journal of Cellular Biochemistry* 105:437-446 (2008).

Maile et al, "Structural Analysis of the Role of the β3 Subunit of the αVβ3 Integrin in IGF-I Signaling" *Journal of Cell Science* 114:1417-1425 (2001).

Maile et al. "The Association Between Integrin-Associated Protein and SHPS-1 Regulates Insulin-Like Growth Factor-I Receptor Signaling in Vascular Smooth Muscle Cells" *Molecular Biology of the Cell* 14:3519-3528 (2003).

Moralez et al, "Insulin-Like Growth Factor Binding Protein-5 (IGFBP-5) Interacts With Thrombospondin-1 to Induce Negative Regulatory Effects on IGF-I Actions" *Journal of Cellular Physiology* 203:328-334 (2005).

Saegusa et al, "The Direct Binding of Insulin-Like Growth Factor-1 (IGF-1) to αVβ3 is Involved in IGF-1 Signaling" *The Journal of Biological Chemistry* 284(36)24106-24114 (2009).

Xiong et al, "Crystal Structure of the Extracellular Segment of Integrin 60 Vβ3" *Science* 294:339-346 (2001).

Bantis et al, Nephrology, 2005, 99:e33-e37.

Chertin et al, Pediatr, 2004, 20:283-289.

Brosius, Exp Diab Res, 2003, 4:225-233.

GenBank Database Accession No. AAA38725.1 "Ig kappa-chain Vk8-Jk1 region, partial [Mus musculus]" Oct. 4, 1994 (2 pages).

GenBank Database Accession No. ABP01832.1 "immunoglobulin alpha heavy chain variable region [Mus musculus]" Mar. 22, 2007 (2 pages).

Gerrity et al. "Diabetes-Induced Accelerated Atherosclerosis in Swine" *Diabetes* 50:1654-1665 (2001).

Maile et al. "A Monoclonal Antibody Against $α_vβ_3$ Integrin Inhibits Development of Atherosclerotic Lesions in Diabetic Pigs" *Science Translational Medicine* 2(18):1-8 (2010).

Qaum et al. "VEGF-initiated blood-retinal barrier breakdown in early diabetes" *Investigative Ophthamology & Visual Science* 42(10):2408-2413 (2001).

Xu et al. "Sensitive blood-retina barrier breakdown quantitation using Evans blue" *Investigative Ophthamology & Visual Science* 42(3):789-794 (2001).

\* cited by examiner

SEQUENCE LISTING

```
<160> NUMBER OF SEQ ID NOS: 82

<210> SEQ ID NO 1
<211> LENGTH: 8
<212> TYPE: PRT
<213> ORGANISM: Artificial
<220> FEATURE:
<223> OTHER INFORMATION: AlphaV beta3 integrin binding sequence from
      IGFBP-5

<400> SEQUENCE: 1

Arg Lys Gly Phe Tyr Lys Arg Lys
1               5

<210> SEQ ID NO 2
<211> LENGTH: 8
<212> TYPE: PRT
<213> ORGANISM: Artificial
<220> FEATURE:
<223> OTHER INFORMATION: Consensus alphaV beta3 integrin binding
      sequence
<220> FEATURE:
<221> NAME/KEY: MISC_FEATURE
<222> LOCATION: (1)..(2)
<223> OTHER INFORMATION: Xaa may be any naturally occurring basic amino
```

```
        acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa may be any naturally occurring aromatic
      amino acid
<220> FEATURE:
<221> NAME/KEY: MISC_FEATURE
<222> LOCATION: (6)..(8)
<223> OTHER INFORMATION: Xaa may be any naturally occurring basic amino
      acid

<400> SEQUENCE: 2

Xaa Xaa Xaa Xaa Xaa Xaa Xaa Xaa
1               5

<210> SEQ ID NO 3
<211> LENGTH: 8
<212> TYPE: PRT
<213> ORGANISM: Artificial
<220> FEATURE:
<223> OTHER INFORMATION: AlphaV beta3 binding sequence from vitronectin

<400> SEQUENCE: 3

Lys Lys Gln Arg Phe Arg His Arg
1               5

<210> SEQ ID NO 4
<211> LENGTH: 17
<212> TYPE: PRT
<213> ORGANISM: Artificial
<220> FEATURE:
<223> OTHER INFORMATION: Synthetic IGF-I agonist
<220> FEATURE:
<221> NAME/KEY: MISC_FEATURE
<222> LOCATION: (1)..(1)
<223> OTHER INFORMATION: Xaa is optionally present and can be any amino
      acid and may be optionally bonded to R1 and R2
<220> FEATURE:
<221> NAME/KEY: MISC_FEATURE
<222> LOCATION: (2)..(5)
<223> OTHER INFORMATION: Xaa is optionally present and can be any amino
      acid
<220> FEATURE:
<221> NAME/KEY: MISC_FEATURE
<222> LOCATION: (6)..(6)
<223> OTHER INFORMATION: Xaa can be any basic amino acid or
      phosphorylated serine
<220> FEATURE:
<221> NAME/KEY: MISC_FEATURE
<222> LOCATION: (7)..(7)
<223> OTHER INFORMATION: Xaa can be any basic amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any aromatic amino acid
<220> FEATURE:
<221> NAME/KEY: MISC_FEATURE
<222> LOCATION: (11)..(12)
<223> OTHER INFORMATION: Xaa can be any basic amino acid
<220> FEATURE:
<221> NAME/KEY: MISC_FEATURE
<222> LOCATION: (13)..(13)
<223> OTHER INFORMATION: Xaa can be any basic amino acid or
      phosphorylated serine
<220> FEATURE:
<221> NAME/KEY: MISC_FEATURE
```

```
<222> LOCATION: (14)..(16)
<223> OTHER INFORMATION: Xaa is optionally present and can be any amino
      acid
<220> FEATURE:
<221> NAME/KEY: MISC_FEATURE
<222> LOCATION: (17)..(17)
<223> OTHER INFORMATION: Xaa is optionally present and can be any amino
      acid and may be optionally bonded to R3 and R4

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 5
<211> LENGTH: 17
<212> TYPE: PRT
<213> ORGANISM: Artificial
<220> FEATURE:
<223> OTHER INFORMATION: Synthetic IGF-I antagonist
<220> FEATURE:
<221> NAME/KEY: MISC_FEATURE
<222> LOCATION: (1)..(1)
<223> OTHER INFORMATION: Xaa is optionally present and can be any amino
      acid and may be optionally bonded to R11 and R12
<220> FEATURE:
<221> NAME/KEY: MISC_FEATURE
<222> LOCATION: (2)..(5)
<223> OTHER INFORMATION: Xaa is optionally present and can be any amino
      acid
<220> FEATURE:
<221> NAME/KEY: MISC_FEATURE
<222> LOCATION: (6)..(7)
<223> OTHER INFORMATION: Xaa is optionally present and can be any basic
      amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any aromatic amino acid
<220> FEATURE:
<221> NAME/KEY: MISC_FEATURE
<222> LOCATION: (11)..(12)
<223> OTHER INFORMATION: Xaa can be any basic amino acid
<220> FEATURE:
<221> NAME/KEY: MISC_FEATURE
<222> LOCATION: (13)..(13)
<223> OTHER INFORMATION: Xaa can be any noncharged, neutral, or
      hydrophobic amino acid
<220> FEATURE:
<221> NAME/KEY: MISC_FEATURE
<222> LOCATION: (14)..(16)
<223> OTHER INFORMATION: Xaa is optionally present and can be any amino
      acid
<220> FEATURE:
<221> NAME/KEY: MISC_FEATURE
<222> LOCATION: (17)..(17)
<223> OTHER INFORMATION: Xaa is optionally present and can be any amino
      acid and may be optionally bonded to R13 and R14

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 6
<211> LENGTH: 8
<212> TYPE: PRT
<213> ORGANISM: Artificial
<220> FEATURE:
```

```
<223> OTHER INFORMATION: Synthetic IGF-I antagonist

<400> SEQUENCE: 6

Lys Lys Gln Arg Phe Arg His Leu
1               5

<210> SEQ ID NO 7
<211> LENGTH: 17
<212> TYPE: PRT
<213> ORGANISM: Artificial
<220> FEATURE:
<223> OTHER INFORMATION: Synthetic IGF-I agonist consensus sequence
<220> FEATURE:
<221> NAME/KEY: MISC_FEATURE
<222> LOCATION: (1)..(5)
<223> OTHER INFORMATION: Xaa is optionally present and can be any amino
      acid
<220> FEATURE:
<221> NAME/KEY: MISC_FEATURE
<222> LOCATION: (6)..(7)
<223> OTHER INFORMATION: Xaa can be arginine, lysine, or histidine
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be phenylalalnine, tyrosine,
      tryptophan, or histidine
<220> FEATURE:
<221> NAME/KEY: MISC_FEATURE
<222> LOCATION: (11)..(13)
<223> OTHER INFORMATION: Xaa can be arginine, lysine, or histidine
<220> FEATURE:
<221> NAME/KEY: MISC_FEATURE
<222> LOCATION: (14)..(17)
<223> OTHER INFORMATION: Xaa is optionally present and can be any amino
      acid

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 8
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 8

Lys Lys Gln Arg Phe Arg His Arg
1               5

<210> SEQ ID NO 9
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 9

Arg Lys Gln Arg Phe Arg His Arg
1               5

<210> SEQ ID NO 10
<211> LENGTH: 8
<212> TYPE: PRT
```

```
<213> ORGANISM: Artificial
<220> FEATURE:
<223> OTHER INFORMATION: Synthetic IGF-I agonist sequence

<400> SEQUENCE: 10

Lys Arg Gln Arg Phe Arg His Arg
1               5

<210> SEQ ID NO 11
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 11

Lys Lys Gln Arg Phe Lys His Arg
1               5

<210> SEQ ID NO 12
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 12

Lys Lys Gln Arg Phe Arg His Lys
1               5

<210> SEQ ID NO 13
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 13

Lys Lys Gln Arg Phe Arg Arg Arg
1               5

<210> SEQ ID NO 14
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 14

Lys Lys Gln Arg Phe Arg Lys Arg
1               5

<210> SEQ ID NO 15
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 15

Lys Lys Gln Arg Phe Arg His Arg
1               5

<210> SEQ ID NO 16
<211> LENGTH: 8
<212> TYPE: PRT
<213> ORGANISM: Artificial
```

```
<220> FEATURE:
<223> OTHER INFORMATION: Synthetic IGF-I agonist sequence

<400> SEQUENCE: 16

His Lys Gln Arg Phe Arg His Arg
1               5

<210> SEQ ID NO 17
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 17

Lys His Gln Arg Phe Arg His Arg
1               5

<210> SEQ ID NO 18
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 18

Arg Arg Gln Arg Phe Arg His Arg
1               5

<210> SEQ ID NO 19
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 19

Lys Lys Gln Arg Phe Lys His Lys
1               5

<210> SEQ ID NO 20
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 20

Lys Lys Gln Lys Phe Arg His Arg
1               5

<210> SEQ ID NO 21
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 21

Lys Lys Asn Arg Phe Arg His Arg
1               5

<210> SEQ ID NO 22
<211> LENGTH: 8
<212> TYPE: PRT
<213> ORGANISM: Artificial
<220> FEATURE:
```

```
<223> OTHER INFORMATION: Synthetic IGF-I agonist sequence

<400> SEQUENCE: 22

Lys Lys Gln Arg Tyr Arg His Arg
1               5

<210> SEQ ID NO 23
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 23

Lys Lys Gln Arg Trp Arg His Arg
1               5

<210> SEQ ID NO 24
<211> LENGTH: 8
<212> TYPE: PRT
<213> ORGANISM: Artificial
<220> FEATURE:
<223> OTHER INFORMATION: Synthetic IGF-I agonist sequence

<400> SEQUENCE: 24

Lys Lys Gln Arg His Arg His Arg
1               5

<210> SEQ ID NO 25
<211> LENGTH: 10
<212> TYPE: PRT
<213> ORGANISM: Artificial
<220> FEATURE:
<223> OTHER INFORMATION: Synthetic IGF-I agonist sequence

<400> SEQUENCE: 25

Ala Lys Lys Gln Arg Phe Arg His Arg Asn
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic IGF-I agonist sequence

<400> SEQUENCE: 26

Leu Ala Lys Lys Gln Arg Phe Arg His Arg Asn Arg
1               5                   10

<210> SEQ ID NO 27
<211> LENGTH: 14
<212> TYPE: PRT
<213> ORGANISM: Artificial
<220> FEATURE:
<223> OTHER INFORMATION: Synthetic IGF-I agonist sequence

<400> SEQUENCE: 27

Ser Leu Ala Lys Lys Gln Arg Phe Arg His Arg Asn Arg Lys
1               5                   10

<210> SEQ ID NO 28
<211> LENGTH: 16
<212> TYPE: PRT
<213> ORGANISM: Artificial
<220> FEATURE:
<223> OTHER INFORMATION: Synthetic IGF-I agonist sequence
```

<400> SEQUENCE: 28

Pro Ser Leu Ala Lys Lys Gln Arg Phe Arg His Arg Asn Arg Lys Gly
1               5                   10                  15

<210> SEQ ID NO 29
<211> LENGTH: 17
<212> TYPE: PRT
<213> ORGANISM: Artificial
<220> FEATURE:
<223> OTHER INFORMATION: Synthetic IGF-I agonist sequence

<400> SEQUENCE: 29

Arg Pro Ser Leu Ala Lys Lys Gln Arg Phe Arg His Arg Asn Arg Lys
1               5                   10                  15
Gly

<210> SEQ ID NO 30
<211> LENGTH: 9
<212> TYPE: PRT
<213> ORGANISM: Artificial
<220> FEATURE:
<223> OTHER INFORMATION: Synthetic IGF-I agonist sequence

<400> SEQUENCE: 30

Ala Lys Lys Gln Arg Phe Arg His Arg
1               5

<210> SEQ ID NO 31
<211> LENGTH: 10
<212> TYPE: PRT
<213> ORGANISM: Artificial
<220> FEATURE:
<223> OTHER INFORMATION: Synthetic IGF-I agonist sequence

<400> SEQUENCE: 31

Leu Ala Lys Lys Gln Arg Phe Arg His Arg
1               5                   10

<210> SEQ ID NO 32
<211> LENGTH: 11
<212> TYPE: PRT
<213> ORGANISM: Artificial
<220> FEATURE:
<223> OTHER INFORMATION: Synthetic IGF-I agonist sequence

<400> SEQUENCE: 32

Ser Leu Ala Lys Lys Gln Arg Phe Arg His Arg
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic IGF-I agonist sequence

<400> SEQUENCE: 33

Pro Ser Leu Ala Lys Lys Gln Arg Phe Arg His Arg
1               5                   10

<210> SEQ ID NO 34
<211> LENGTH: 13
<212> TYPE: PRT
<213> ORGANISM: Artificial
<220> FEATURE:

<223> OTHER INFORMATION: Synthetic IGF-I agonist sequence

<400> SEQUENCE: 34

Arg Pro Ser Leu Ala Lys Lys Gln Arg Phe Arg His Arg
1               5                   10

<210> SEQ ID NO 35
<211> LENGTH: 9
<212> TYPE: PRT
<213> ORGANISM: Artificial
<220> FEATURE:
<223> OTHER INFORMATION: Synthetic IGF-I agonist sequence

<400> SEQUENCE: 35

Lys Lys Gln Arg Phe Arg His Arg Asn
1               5

<210> SEQ ID NO 36
<211> LENGTH: 10
<212> TYPE: PRT
<213> ORGANISM: Artificial
<220> FEATURE:
<223> OTHER INFORMATION: Synthetic IGF-I agonist sequence

<400> SEQUENCE: 36

Lys Lys Gln Arg Phe Arg His Arg Asn Arg
1               5                   10

<210> SEQ ID NO 37
<211> LENGTH: 11
<212> TYPE: PRT
<213> ORGANISM: Artificial
<220> FEATURE:
<223> OTHER INFORMATION: Synthetic IGF-I agonist sequence

<400> SEQUENCE: 37

Lys Lys Gln Arg Phe Arg His Arg Asn Arg Lys
1               5                   10

<210> SEQ ID NO 38
<211> LENGTH: 12
<212> TYPE: PRT
<213> ORGANISM: Artificial
<220> FEATURE:
<223> OTHER INFORMATION: Synthetic IGF-I agonist sequence

<400> SEQUENCE: 38

Lys Lys Gln Arg Phe Arg His Arg Asn Arg Lys Gly
1               5                   10

<210> SEQ ID NO 39
<211> LENGTH: 14
<212> TYPE: PRT
<213> ORGANISM: Artificial
<220> FEATURE:
<223> OTHER INFORMATION: Synthetic IGF-I agonist sequence

<400> SEQUENCE: 39

Arg Pro Ser Leu Ala Lys Lys Gln Arg Phe Arg His Arg Asn
1               5                   10

<210> SEQ ID NO 40
<211> LENGTH: 15
<212> TYPE: PRT
<213> ORGANISM: Artificial
<220> FEATURE:
<223> OTHER INFORMATION: Synthetic IGF-I agonist sequence

<400> SEQUENCE: 40

Arg Pro Ser Leu Ala Lys Lys Gln Arg Phe Arg His Arg Asn Arg
1               5                   10                  15

<210> SEQ ID NO 41
<211> LENGTH: 16
<212> TYPE: PRT
<213> ORGANISM: Artificial
<220> FEATURE:
<223> OTHER INFORMATION: Synthetic IGF-I agonist sequence

<400> SEQUENCE: 41

Arg Pro Ser Leu Ala Lys Lys Gln Arg Phe Arg His Arg Asn Arg Lys
1               5                   10                  15

<210> SEQ ID NO 42
<211> LENGTH: 13
<212> TYPE: PRT
<213> ORGANISM: Artificial
<220> FEATURE:
<223> OTHER INFORMATION: Synthetic IGF-I agonist sequence

<400> SEQUENCE: 42

Ala Lys Lys Gln Arg Phe Arg His Arg Asn Arg Lys Gly
1               5                   10

<210> SEQ ID NO 43
<211> LENGTH: 14
<212> TYPE: PRT
<213> ORGANISM: Artificial
<220> FEATURE:
<223> OTHER INFORMATION: Synthetic IGF-I agonist sequence

<400> SEQUENCE: 43

Leu Ala Lys Lys Gln Arg Phe Arg His Arg Asn Arg Lys Gly
1               5                   10

<210> SEQ ID NO 44
<211> LENGTH: 15
<212> TYPE: PRT
<213> ORGANISM: Artificial
<220> FEATURE:
<223> OTHER INFORMATION: Synthetic IGF-I agonist sequence

<400> SEQUENCE: 44

Ser Leu Ala Lys Lys Gln Arg Phe Arg His Arg Asn Arg Lys Gly
1               5                   10                  15

<210> SEQ ID NO 45
<211> LENGTH: 17
<212> TYPE: PRT
<213> ORGANISM: Artificial
<220> FEATURE:
<223> OTHER INFORMATION: IGF-I antagonist consensus sequence
<220> FEATURE:
<221> NAME/KEY: MISC_FEATURE
<222> LOCATION: (1)..(5)
<223> OTHER INFORMATION: Xaa is optionally present and can be any amino
      acid
<220> FEATURE:
<221> NAME/KEY: MISC_FEATURE
<222> LOCATION: (6)..(7)
<223> OTHER INFORMATION: Xaa can be arginine, lysine, or histidine
<220> FEATURE:
<221> NAME/KEY: MISC_FEATURE
<222> LOCATION: (8)..(9)
<223> OTHER INFORMATION: Xaa can be any amino acid
<220> FEATURE:

```
<221> NAME/KEY: MISC_FEATURE
<222> LOCATION: (10)..(10)
<223> OTHER INFORMATION: Xaa can be phenylalanine, tyrosine, tryptophan,
      or histidine
<220> FEATURE:
<221> NAME/KEY: MISC_FEATURE
<222> LOCATION: (11)..(12)
<223> OTHER INFORMATION: Xaa can be arginine, lysine, or histidine
<220> FEATURE:
<221> NAME/KEY: MISC_FEATURE
<222> LOCATION: (13)..(13)
<223> OTHER INFORMATION: Xaa can be isoeucine, leucine, valine,
      methionine, phenylalanine, tryptophan, or cysteine
<220> FEATURE:
<221> NAME/KEY: MISC_FEATURE
<222> LOCATION: (14)..(17)
<223> OTHER INFORMATION: Xaa is optionally present and can be any amino
      acid

<400> SEQUENCE: 45

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 46
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 46

Lys Lys Gln Arg Phe Arg His Leu
1               5

<210> SEQ ID NO 47
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 47

Lys Lys Gln Arg Phe Arg His Ala
1               5

<210> SEQ ID NO 48
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 48

Arg Lys Gly Arg Tyr Lys Arg Ala
1               5

<210> SEQ ID NO 49
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 49

Lys Lys Gln Arg Phe Arg His Ile
1               5
```

```
<210> SEQ ID NO 50
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 50

Lys Lys Gln Arg Phe Arg His Val
1               5

<210> SEQ ID NO 51
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 51

Lys Lys Gln Arg Phe Arg His Met
1               5

<210> SEQ ID NO 52
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 52

Lys Lys Gln Arg Phe Arg His Cys
1               5

<210> SEQ ID NO 53
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 53

Lys Lys Gln Arg Phe Arg His Phe
1               5

<210> SEQ ID NO 54
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 54

Lys Lys Gln Arg Phe Arg His Trp
1               5

<210> SEQ ID NO 55
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 55

Arg Lys Gln Arg Phe Arg His Leu
1               5

<210> SEQ ID NO 56
```

```
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 56

Arg Lys Gln Arg Phe Arg His Ile
1               5

<210> SEQ ID NO 57
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 57

Arg Lys Gln Arg Phe Arg His Val
1               5

<210> SEQ ID NO 58
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 58

Arg Lys Gln Arg Phe Arg His Met
1               5

<210> SEQ ID NO 59
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 59

Arg Lys Gln Arg Phe Arg His Cys
1               5

<210> SEQ ID NO 60
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 60

Arg Lys Gln Arg Phe Arg His Phe
1               5

<210> SEQ ID NO 61
<211> LENGTH: 8
<212> TYPE: PRT
<213> ORGANISM: Artificial
<220> FEATURE:
<223> OTHER INFORMATION: Synthetic IGF-I antagonist sequence

<400> SEQUENCE: 61

Arg Lys Gln Arg Phe Arg His Trp
1               5

<210> SEQ ID NO 62
<211> LENGTH: 10
```

```
<212> TYPE: PRT
<213> ORGANISM: Artificial
<220> FEATURE:
<223> OTHER INFORMATION: Synthetic IGF-I antagonist sequence

<400> SEQUENCE: 62

Ala Lys Lys Gln Arg Phe Arg His Leu Asn
1               5                   10

<210> SEQ ID NO 63
<211> LENGTH: 12
<212> TYPE: PRT
<213> ORGANISM: Artificial
<220> FEATURE:
<223> OTHER INFORMATION: Synthetic IGF-I antagonist sequence

<400> SEQUENCE: 63

Leu Ala Lys Lys Gln Arg Phe Arg His Leu Asn Arg
1               5                   10

<210> SEQ ID NO 64
<211> LENGTH: 14
<212> TYPE: PRT
<213> ORGANISM: Artificial
<220> FEATURE:
<223> OTHER INFORMATION: Synthetic IGF-I antagonist sequence

<400> SEQUENCE: 64

Ser Leu Ala Lys Lys Gln Arg Phe Arg His Leu Asn Arg Lys
1               5                   10

<210> SEQ ID NO 65
<211> LENGTH: 16
<212> TYPE: PRT
<213> ORGANISM: Artificial
<220> FEATURE:
<223> OTHER INFORMATION: Synthetic IGF-I antagonist sequence

<400> SEQUENCE: 65

Pro Ser Leu Ala Lys Lys Gln Arg Phe Arg His Leu Asn Arg Lys Gly
1               5                   10                  15

<210> SEQ ID NO 66
<211> LENGTH: 17
<212> TYPE: PRT
<213> ORGANISM: Artificial
<220> FEATURE:
<223> OTHER INFORMATION: Synthetic IGF-I antagonist sequence

<400> SEQUENCE: 66

Arg Pro Ser Leu Ala Lys Lys Gln Arg Phe Arg His Leu Asn Arg Lys
1               5                   10                  15

Gly

<210> SEQ ID NO 67
<211> LENGTH: 9
<212> TYPE: PRT
<213> ORGANISM: Artificial
<220> FEATURE:
<223> OTHER INFORMATION: Synthetic IGF-I antagonist sequence

<400> SEQUENCE: 67

Ala Lys Lys Gln Arg Phe Arg His Leu
1               5

<210> SEQ ID NO 68
```

```
<211> LENGTH: 10
<212> TYPE: PRT
<213> ORGANISM: Artificial
<220> FEATURE:
<223> OTHER INFORMATION: Synthetic IGF-I antagonist sequence

<400> SEQUENCE: 68

Leu Ala Lys Lys Gln Arg Phe Arg His Leu
1               5                   10

<210> SEQ ID NO 69
<211> LENGTH: 11
<212> TYPE: PRT
<213> ORGANISM: Artificial
<220> FEATURE:
<223> OTHER INFORMATION: Synthetic IGF-I antagonist sequence

<400> SEQUENCE: 69

Ser Leu Ala Lys Lys Gln Arg Phe Arg His Leu
1               5                   10

<210> SEQ ID NO 70
<211> LENGTH: 12
<212> TYPE: PRT
<213> ORGANISM: Artificial
<220> FEATURE:
<223> OTHER INFORMATION: Synthetic IGF-I antagonist sequence

<400> SEQUENCE: 70

Pro Ser Leu Ala Lys Lys Gln Arg Phe Arg His Leu
1               5                   10

<210> SEQ ID NO 71
<211> LENGTH: 13
<212> TYPE: PRT
<213> ORGANISM: Artificial
<220> FEATURE:
<223> OTHER INFORMATION: Synthetic IGF-I antagonist sequence

<400> SEQUENCE: 71

Arg Pro Ser Leu Ala Lys Lys Gln Arg Phe Arg His Leu
1               5                   10

<210> SEQ ID NO 72
<211> LENGTH: 9
<212> TYPE: PRT
<213> ORGANISM: Artificial
<220> FEATURE:
<223> OTHER INFORMATION: Synthetic IGF-I antagonist sequence

<400> SEQUENCE: 72

Lys Lys Gln Arg Phe Arg His Leu Asn
1               5

<210> SEQ ID NO 73
<211> LENGTH: 10
<212> TYPE: PRT
<213> ORGANISM: Artificial
<220> FEATURE:
<223> OTHER INFORMATION: Synthetic IGF-I antagonist sequence

<400> SEQUENCE: 73

Lys Lys Gln Arg Phe Arg His Leu Asn Arg
1               5                   10

<210> SEQ ID NO 74
<211> LENGTH: 11
```

```
<212> TYPE: PRT
<213> ORGANISM: Artificial
<220> FEATURE:
<223> OTHER INFORMATION: Synthetic IGF-I antagonist sequence

<400> SEQUENCE: 74

Lys Lys Gln Arg Phe Arg His Leu Asn Arg Lys
1               5                   10

<210> SEQ ID NO 75
<211> LENGTH: 12
<212> TYPE: PRT
<213> ORGANISM: Artificial
<220> FEATURE:
<223> OTHER INFORMATION: Synthetic IGF-I antagonist sequence

<400> SEQUENCE: 75

Lys Lys Gln Arg Phe Arg His Leu Asn Arg Lys Gly
1               5                   10

<210> SEQ ID NO 76
<211> LENGTH: 14
<212> TYPE: PRT
<213> ORGANISM: Artificial
<220> FEATURE:
<223> OTHER INFORMATION: Synthetic IGF-I antagonist sequence

<400> SEQUENCE: 76

Arg Pro Ser Leu Ala Lys Lys Gln Arg Phe Arg His Leu Asn
1               5                   10

<210> SEQ ID NO 77
<211> LENGTH: 15
<212> TYPE: PRT
<213> ORGANISM: Artificial
<220> FEATURE:
<223> OTHER INFORMATION: Synthetic IGF-I antagonist sequence

<400> SEQUENCE: 77

Arg Pro Ser Leu Ala Lys Lys Gln Arg Phe Arg His Leu Asn Arg
1               5                   10                  15

<210> SEQ ID NO 78
<211> LENGTH: 16
<212> TYPE: PRT
<213> ORGANISM: Artificial
<220> FEATURE:
<223> OTHER INFORMATION: Synthetic IGF-I antagonist sequence

<400> SEQUENCE: 78

Arg Pro Ser Leu Ala Lys Lys Gln Arg Phe Arg His Leu Asn Arg Lys
1               5                   10                  15

<210> SEQ ID NO 79
<211> LENGTH: 13
<212> TYPE: PRT
<213> ORGANISM: Artificial
<220> FEATURE:
<223> OTHER INFORMATION: Synthetic IGF-I antagonist sequence

<400> SEQUENCE: 79

Ala Lys Lys Gln Arg Phe Arg His Leu Asn Arg Lys Gly
1               5                   10

<210> SEQ ID NO 80
<211> LENGTH: 14
<212> TYPE: PRT
```

```
<213> ORGANISM: Artificial
<220> FEATURE:
<223> OTHER INFORMATION: Synthetic IGF-I antagonist sequence

<400> SEQUENCE: 80

Leu Ala Lys Lys Gln Arg Phe Arg His Leu Asn Arg Lys Gly
1               5                   10

<210> SEQ ID NO 81
<211> LENGTH: 15
<212> TYPE: PRT
<213> ORGANISM: Artificial
<220> FEATURE:
<223> OTHER INFORMATION: Synthetic IGF-I antagonist sequence

<400> SEQUENCE: 81

Ser Leu Ala Lys Lys Gln Arg Phe Arg His Leu Asn Arg Lys Gly
1               5                   10                  15

<210> SEQ ID NO 82
<211> LENGTH: 8
<212> TYPE: PRT
<213> ORGANISM: Artificial
<220> FEATURE:
<223> OTHER INFORMATION: Beta3 cysteine loop peptide

<400> SEQUENCE: 82

Cys Tyr Asp Met Lys Thr Thr Cys
1               5
```

MONOCLONAL ANTIBODIES FOR ENHANCING OR INHIBITING INSULIN-LIKE GROWTH FACTOR-I

RELATED APPLICATIONS

This application is a continuation application of, and claims priority to, U.S. patent application Ser. No. 12/498,719, filed Jul. 7, 2009 (U.S. Pat. No. 8,187,595 issued May 29, 2012), which is a continuation-in-part application of U.S. patent application Ser. No. 11/123,290, filed May 6, 2005 (U.S. Pat. No. 7,723,483, issued May 25, 2010), which claims the benefit of U.S. Provisional Patent Application Ser. No. 60/657,151, filed Feb. 28, 2005, and U.S. Provisional Patent Application Ser. No. 60/569,147, filed May 7, 2004, the disclosures of all of which are incorporated by reference herein in their entirety.

STATEMENT OF GOVERNMENT SUPPORT

This invention was made with government support under grant number AG-02331 awarded by the National Institutes of Health. The government has certain rights in the invention.

FIELD OF THE INVENTION

This invention describes methods for inhibiting or enhancing the actions of insulin-like growth factor-I (IGF-I).

BACKGROUND OF THE INVENTION

IGF-I is a small polypeptide hormone that stimulates the growth of all types of cells. Because IGF-I has a broad spectrum of action and stimulates balanced tissue growth it has been implicated in the development of several important human cancers and also in atherosclerosis. IGF-I acts primarily on anchorage dependent cells that are contained in these tissues. These cells also possess a class of receptors termed integrin receptors which are responsible for their attachment to extracellular matrix molecules. In order for cells to divide normally, in response to extracellular stimuli the cell has to sense that its integrin receptors are bound to extracellular matrix molecules. Therefore manipulation of ligand occupancy of integrin receptors can alter processes that are important in disease development such as cell division and migration.

Our studies have determined that IGF-I stimulates endothelial and smooth muscle cell division. They have further determined that these cells utilize the αVβ3 integrin receptor to communicate to the cell nucleus that they are adhered adequately to extracellular matrix in order to divide. The abundance of one specific integrin (the αVβ3 integrin) is relatively restricted in human tissues and it is expressed primarily in growing cells and particularly in cells involved in the maintenance of the vasculature such as smooth muscle and endothelial cells. Our studies have shown that occupancy of this integrin receptor with its naturally occurring ligands such as osteopontin, vitronectin and thrombospondin is required for these cells to respond to IGF-I with increased DNA synthesis and cell migration. Blocking ligand occupancy of this integrin with disintegrin antagonists results in inhibition of cell growth and migration. Our studies have shown that this cooperative interaction between αVβ3 and the IGF-I receptor is mediated by regulating the translocation of two specific signaling molecules. These molecules are 1) a protein tyrosine phosphatase termed SHP-2 and 2) a signaling protein termed Shc. Under normal circumstances SHP-2 is localized in the cytoskeleton and cytosolic compartments of the cell. Following ligand occupancy of αVβ3 the cytoplasmic domain of the β3 integrin undergoes tyrosine phosphorylation. SHP-2 is transferred to the cell membrane by binding to proteins that bind to the phosphorylated tyrosine residues in β3. This transfer is necessary in order to localize SHP-2 to the membrane where it recruits other important signaling molecules such as Shc. SHP-2 colocalization with Shc and/or dephosphorylation of signaling molecules within the IGF-I signaling pathway is required for their activation and for subsequent transmission of signals from the IGF-I receptor to nucleus. Activation of the two major intracellular signaling pathways that are required for IGF-I activation (e.g. the PI-3 kinase and MAP kinase pathways) can be inhibited by inhibiting either SHP-2 or Shc transfer to the membrane. The site of localization of SHP-2 and Shc is a membrane protein termed SHPS-1. SHPS-1 is phosphorylated in response to IGF-I. This phosphorylation is required for SHP-2 and for Shc transfer. Shc is phosphorylated after transfer to SHPS-1. Blocking αVβ3 ligand occupancy blocks both SHP-2 and Shc transfer thus inhibiting IGF-I stimulated cell growth.

Although methods have been described previously for inhibiting ligand occupancy of the αVβ3 integrin, they all utilize a technology that inhibits binding to a specific binding site on the αVβ3 heterodimer that binds to the arginine, glycine, asparagine (RGD) sequence within the ECM ligands. Binding αVβ3 antagonists to this site is associated with drug toxicity and side effects. Accordingly there is a need for new ways to inhibit, or activate, IGF-1 actions that do not utilize the αVβ3 binding site that binds to the RGD sequence.

SUMMARY OF THE INVENTION

In our invention we have determined that there is a second binding site on αVβ3 that binds to several extracellular matrix proteins. More importantly we have determined that enhancing ligand occupancy of this domain augments IGF-I signaling and inhibiting ligand occupancy of this specific domain, inhibits IGF-I actions. Importantly ligand occupancy of this second binding site does not stimulate the specific biochemical events that are stimulated by peptides that bind to the RGD binding site.

A first aspect of the present invention is an αVβ3 integrin extracellular matrix protein binding site (or cysteine loop domain contained in amino acids 177-184 of the β33 subunit) antagonist (e.g., a peptide antagonist or analog thereof or antibody that binds the cysteine loop domain).

A particular embodiment of the foregoing is an antibody that specifically binds to the αVβ3 integrin extracellular matrix protein binding site (or cysteine loop domain) (e.g., specifically binds to the cysteine loop domain at amino acids 177 to 184 of a human β3 integrin; optionally but preferably does not specifically bind the RGD binding site of a human β3 integrin; and optionally but preferably specifically binds to the cysteine loop domain at amino acids 177 to 184 of a pig β3 integrin. In some embodiments, the antibody is (a) the monoclonal antibody produced by hybridoma LAM-CLOOP-101, or (b) a monoclonal antibody that competes for binding to the same epitope as the epitope bound by a monoclonal antibody produced by the hybridoma LAM-CLOOP-101 (i.e., a monoclonal antibody that specifically binds to the epitope bound by a monoclonal antibody produced by the hybridoma LAM-CLOOP-101.

A second aspect of the present invention is an αVβ3 integrin extracellular matrix protein binding site (or cysteine loop domain) agonist (e.g., a peptide agonist or analog thereof).

A further aspect of the present invention is a pharmaceutical formulation comprising an active agent as described herein in a pharmaceutically acceptable carrier.

A further aspect of the present invention is a method of inhibiting IGF-1 actions in a subject in need thereof, comprising administering said subject an αVβ3 integrin extracellular matrix protein binding site (or cysteine loop domain) antagonist in an amount effective to inhibit IGF-1 actions in said subject. For example, the subject may be afflicted with a tumor (e.g., breast cancer tumors, colon cancer tumors, lung cancer tumors, and prostate cancer tumors, and the antagonist administered in an amount effective to treat the tumor. In some embodiments, the tumor or blood vessels supplying the tumor expresses αVβ3 receptors.

In another example, the subject is afflicted with atherosclerosis (e.g., coronary atherosclerosis), and the antagonist is administered in an amount effective to treat the atherosclerosis. In some embodiments the atherosclerosis is characterized by atherosclerotic lesion cells that express αVβ3 receptors. In another example the subject is afflicted with osteoporosis, and the antagonist is administered in an amount effective to treat the osteoporosis.

In another example the subject is afflicted with pathological angiogenesis (e.g., vascularization of a tumor, including tumors that do express levels of integrin αVβ3 detectable by immunohistochemistry and tumors that do not express levels of integrin αVβ3 detectable by immunohistochemistry), and the antagonist is administered in an amount effective to treat the pathological angiogenesis.

In another example, the subject is afflicted with diabetes (e.g., type I diabetes, type II diabetes, diabetic retinopathy, diabetic nephropathy), and the antagonist is administered in an amount effective to treat these complications of diabetes.

An aspect of the invention is, in a method of treating a tumor in a subject in need thereof by administering αVβ3 treatment effective amount of an antineoplastic compound or radiation therapy to the subject, the improvement comprising administering to the subject an αVβ3 integrin cysteine loop domain antagonist in an amount effective to inhibit IGF-I action in the subject (e.g., and thereby enhance the activity of the antineoplastic compound or radiation therapy to the subject, inhibit bone loss in the subject, or both) Subjects may be afflicted with tumors such as breast cancer tumors, colon cancer tumors, lung cancer tumors, and prostate cancer tumors. In some embodiments the tumor expresses αVβ3 receptors.

A still further aspect of the present invention is a method of enhancing IGF-1 action in a subject in need thereof, comprising administering said subject an αVβ3 integrin cysteine loop domain agonist in an amount effective to enhance IGF-1 action in the subject. For example, the subject (e.g., infant, juvenile or juvenile subjects) may be afflicted with insufficient growth, and the agonist administered in an amount effective to enhance the growth of the subject. In another example the subject (e.g., an infant subject) is afflicted with defective retinal vascularization, and the agonist is administered in an amount effective to treat the defective retinal vascularization. In another example, the subject is afflicted with an ischemic injury (e.g., peripheral vascular disease with claudication, myocardial infarction, etc.), and the agonist is administered in an amount effective to treat the ischemic injury. In another embodiment the subject is afflicted with neuronal atrophy or failure of neural process development, and the agonist is administered in an amount effective to treat the neuronal atrophy or facilitate neural process development. In another embodiment the subject (e.g., an adult or geriatric subject) is afflicted with a hip fracture and the agonist is administered in an amount effective to treat the hip fracture. In another embodiment the subject is afflicted with a diabetic ischemic ulcer, and the agonist is administered in an amount effective to treat the diabetic ischemic ulcer.

A further aspect of the present invention is the use of an active agent as described herein for the manufacture of a medicament for carrying out a method of treatment as described herein.

A further aspect of the invention is a computer-based method for identifying compounds that modulate activity of IGF-1, comprising: (a) providing a plurality of coordinates (e.g., at least 20, 30 or 40 coordinates) for the cysteine loop domain (amino acids 177-184) of an αVβ3 integrin in a computer; (b) providing a structure of a candidate compound to the computer in computer readable form; and (c) determining whether or not the candidate compound fits into or docks with a binding cavity of the cysteine loop domain, wherein a candidate compound that fits or docks into the binding cavity is determined to be likely to modulate activity of IGF-1.

A further aspect of the invention computer-based method for rationally designing a compound that modulates activity of IGF-1, comprising: (a) generating a computer readable model of an extacellular matrix protein binding site of an αVβ3 integrin; and then (b) designing in a computer with the model a compound having a structure and a charge distribution compatible with the binding site, the compound having a functional group that interacts with the binding site to modulate acetyl-CoA carboxylase activity.

In one embodiment the present invention provides a method of screening compounds for activity in modulating cellular activation by IGF-1, comprising the steps of: (a) contacting, preferably in vitro, a test compound to a system comprising a β3 integrin; then (b) determining whether the test compound binds to the cysteine loop at amino acids 177 to 184 of the β3 integrin; and then (c) identifying the test compound as active in modulating cellular activation by IGF-1 if the compound binds the cysteine loop domain. In some embodiments the test system comprises αVβ3 integrin as a complex. The determining step may be carried out by any suitable means, such as by determining whether or not the test compound inhibits the binding of an antibody, agonist or antagonist as described herein that specifically binds to the cysteine loop domain. The integrin is preferably a mammalian β3 integrin, such as human or pig β3 integrin.

Another embodiment of the present invention provides a method of screening compounds for activity in modulating cellular activation by IGF-1, comprising the steps of: (a) contacting, preferably in vitro, a test compound to a cysteine loop domain, wherein the cysteine loop domain is a peptide comprising amino acids 177 to 184 of a β3 integrin; then (b) determining whether the test compound binds to the cysteine loop domain; (c) identifying the test compound as active in activating cellular activation by IGF-1 if the compound binds the cysteine loop domain. The peptide may consist of not more than 8, 10, 15 or 20 amino acids, and includes amino acids 177-184 of the β3 integrin in sequence. In some embodiments the cysteine loop domain is in solution; in some embodiments the cysteine loop domain is immobilized on a solid support (e.g., as an affinity column). The determining step may be carried out by determining whether or not the test compound inhibits the binding of an antibody, agonist or antagonist as described herein that specifically binds to the cysteine loop domain. Again the integrin is preferably a mammalian β3 integrin such as human or pig β3 integrin. In some embodiments the peptide comprising amino acids 177 to 184 of a β3 integrin.

The present invention is explained in greater detail in the following non-limiting Examples.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

In general, the present invention encompasses a technology to specifically inhibit ligand occupancy of the αVβ3 integrin through an alternative binding site that does not lead to activation of specific intracellular signaling events that can lead to drug toxicity. Administration of antagonists that inhibit the binding of vitronectin to this alternative αVβ3 binding site has been shown to block IGF-I stimulated activation of PI-3 kinase, MAP kinase, DNA synthesis and cell migration. All of these events are important for IGF-I to stimulate smooth muscle cell growth within atherosclerotic lesions. Similarly intestinal smooth muscle cells express this integrin so inhibiting IGF-I actions in this cell type could be useful in the treatment of inflammatory bowel disease. We have also shown that this technology is useful for inhibiting ligand binding to this site on αVβ3 that is expressed on the surface of endothelial cells therefore antagonists that inhibit ligand binding will likely inhibit IGF-I signaling and therefore could be effective treatments of diabetic retinopathy and for angiogenesis that is associated with tumor formation. The invention involves the development of compounds that inhibit binding and can function as competitive antagonists for binding of ECM ligands that bind to this binding site on the αVβ3 integrin.

This invention helps address two major problems in drug development that have inhibited progress in this field. The first problem concerns the IGF-I receptor. While monoclonal antibodies have been developed that inhibit ligand binding to the 1GF-I receptor, the molecular radius of the binding site on the receptor is large therefore inhibiting ligand binding to the IGF-I receptor is a difficult problem in drug development because of the size of the molecule that will be necessary to fully inhibit binding. This invention in contrast inhibits binding to a very small binding site on the αVβ3 integrin. The actual binding site on the integrin itself is encompassed by 8 amino acids and the minimum peptide which is effective inhibiting binding is 8 amino acids therefore the molecular radius of the binding site is substantially smaller than the ligand binding site to the IGF-I receptor and it is of a size that small molecular weight antagonists can be developed. A second problem with antagonizing the IGF-I receptor is that it is ubiquitously present on all cells. Therefore if a strategy were formulated to inhibit IGF-I receptor activity and this were used in combination with therapies that stimulate apoptosis (e.g. a cancer chemotherapeutic or an antiangiogenesis drug) inhibiting IGF-I action in normal cells could also be associated with extensive apoptosis of normal cell types such as GI epithelium, bone marrow precursor cells and neurons. Therefore the toxicity of a coadministered agent would be greatly amplified. Similarly administering IGF-I receptor antagonist even without a coadministered agent is likely to lead to inhibition of protein synthesis and possibly to apoptosis in normal cell types. In contrast this drug will selectively target the αVβ3 integrin. Because αVβ3 integrins that signal cooperatively with the IGF-I receptor are present on vascular endothelial and smooth muscle cells and are usually only expressed in high concentrations in proliferating cells, the compound being developed is quite selective since it specifically targets these cell types. Cell types such as GI epithelium and bone marrow precursor cells which do not express abundant αVβ3 integrin will likely be spared toxicity. Therefore the invention solves the problem of being able to develop low molecular weight inhibitors that inhibit IGF-I action. Secondly it addresses a major problem of generalized toxicity that would be apparent with any anti-IGF-I receptor antagonists. Third, it addresses the problem of inhibiting the IGF-I receptor tyrosine kinase which leads to inhibition of the insulin receptor tyrosine kinase and the development of diabetes.

Enhancing IGF-I action provides beneficial effects in several disease states. Certain neurologic diseases, such as amyotrophic lateral sclerosis have been shown to be partially responsive to IGF-I. Similarly since glucose toxicity in neurons is inhibited by IGF-I then diseases such as diabetic neuropathy may be able to be treated with agents that enhance ligand occupancy of αVβ3 since this is at times expressed on glial cells which provide trophic support for regenerating neurons. It is also possible that a small molecule agonist given with IGF-I would stimulate wound healing or endothelial cell growth within vascular grafts.

A. Definitions

Subjects that may be treated by the present invention include both human subjects for medical purposes and animal subjects for veterinary and drug screening and development purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile and adult subjects.

Amino acid as used herein refers to a compound having a free carboxyl group and a free unsubstituted amino group on the a carbon, which may be joined by peptide bonds to form a peptide active agent as described herein. Amino acids may be standard or non-standard, natural or synthetic, with examples (and their abbreviations) including but not limited to:

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline Ser=S=Serine
Thr=T=Threonine
Trp=W=Tryptophan
Tyr=Y=Tyrosine
Val=V=Valine
Orn=Ornithine
Nal=2-napthylalanine
Nva=Norvaline
Nle=Norleucine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=α-aminonormalbutyric acid
Dip=2,2-diphenylalanine
Thz=4-Thiazolylalanine All peptide sequences mentioned herein are written according to the usual convention whereby the N-terminal amino acid is on the left and the C-terminal amino acid is on the right. A short line (or no line) between two amino acid residues indicates a peptide bond.

"Basic amino acid" refers to any amino acid that is positively charged at a pH of 6.0, including but not limited to R, K, and H.

"Aromatic amino acid" refers to any amino acid that has an aromatic group in the side-chain coupled to the alpha carbon, including but not limited to F, Y, W, and H.

"Hydrophobic amino acid" refers to any amino acid that has a hydrophobic side chain coupled to the alpha carbon, including but not limited to I, L, V, M, F, W and C, most preferably I, L, and V.

"Neutral amino acid" refers to a non-charged amino acid, such as M, F, W, C and A.

"αVβ3 integrin cysteine loop domain" as used herein refers to a specific region on the αVβ3 integrin receptor (particularly mammalian receptors, e.g., those found endogenously in the subject being treated) that has not been identified previously as a region that would result in receptor activation, and specifically excludes the RGD binding domain. Agonists that bind in this region include those containing a region of sequence that is commonly termed a heparin binding domain. In general the cysteine loop domain or region of αVβ3 is occurring between amino acids at positions 177 and 183 within the β3 subunit. See, e.g., B. Vogel et al., A novel integrin specificity exemplified by binding of the alpha v beta 5 integrin to the basic domain of the HIV Tat protein and vitronectin., *J. Cell Biol.* 121: 461-8 (1993).

"IGF-I" as used herein means insulin-like growth factor-I.

"Treat" as used herein refers to any type of treatment or prevention that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms." to any type of treatment that imparts a benefit to a patient afflicted with a disease, including improvement in the condition of the patient (e.g., in one or more symptoms), delay in the progression of the disease, etc.

"Treatment effective amount", "amount effective to treat" or the like as used herein means an amount of the inventive antagonist sufficient to produce a desirable effect upon a patient inflicted with cancer, tumors, atherosclerosis, retinopathy, diabetic neuropathy, or other undesirable medical condition in which IGF-I is inducing abnormal cellular growth. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Antibody" or "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, or human, or may be chimeric or humanized antibodies. The term "antibody" as used herein includes antibody fragments which retain the capability of binding to a target antigen, for example, Fab, $F(ab')_2$, and Fv fragments, and the corresponding fragments obtained from antibodies other than IgG. Such fragments are also produced by known techniques. In some embodiments antibodies may be coupled to or conjugated to a detectable group or therapeutic group in accordance with known techniques.

"Therapeutic group" means any suitable therapeutic group, including but not limited to radionuclides, chemotherapeutic agents and cytotoxic agents.

"Radionuclide" as described herein may be any radionuclide suitable for delivering a therapeutic dosage of radiation to a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$I, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117}$mSn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Chemotherapeutic agent" as used herein includes but is not limited to methotrexate, daunomycin, mitomycin, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamoxifen, paclitaxel, vincristin, vinblastine, camptothecin, actinomycin D, and cytarabine "Cytotoxic agent" as used herein includes but is not limited to ricin (or more particularly the ricin A chain), aclacinomycin, diphtheria toxin. Monensin, Verrucarin A, Abrin, Vinca alkaloids, Tricothecenes, and *Pseudomonas* exotoxin A.

"Detectable group" as used herein includes any suitable detectable group, such as radiolabels (e.g. $^{35}$S, $^{125}$I, $^{131}$I, etc.), enzyme labels (e.g., horseradish peroxidase, alkaline phosphatase, eta), fluorescent labels (e.g., fluorescein, green fluorescent protein, etc.), etc., as used in accordance with known techniques.

"Modulator" as used herein refers to a compound that binds to the indicated binding site (e.g., specifically binds to the cysteine loop of β3) and is an agonist or antagonist, or binds to an adjacent site and thereby affects binding at the cysteine loop of β3domain (e.g., an allosteric inhibitor).

Applicants specifically intend that all United States patent references cited herein be incorporated herein by reference in their entirety.

B. Agonists and Antagonists

Agonists and antagonists that may be used as active agents in carrying out the present invention may be in the form of a variety of different structures, as described further below. In general, the agonist binds to a specific region on the αVβ3 integrin receptor that has not been identified previously as a region that would result in receptor activation. All agonists that we have determined to bind in this region contain a region of sequence that is commonly termed a heparin binding domain. This heparin binding domain is present in 5 ligands that we have found to date that bind to this region of αVβ3. The documentation that they bind to a specific region of αVβ3 has been provided by two types of experiments, as discussed in Example 1 below.

The essential ligand structure of a preferred group of agonists is generally comprised by 8 amino acids. The five ligands that have been shown to bind are connective tissue growth factor, heparin binding epidermal growth factor, vitronectin, osteopontin and insulin-like binding protein-5 (IGFBP-5) (SEQ ID NO: 1). Each of these ligands has the following sequence: BBXXABBB (SEQ ID NO:2) (B=basic, A=aromatic, X=Any). Using mutagenesis of these peptides, we have conducted multiple experiments to determine the residues that are underlined are absolutely required for activity. Substitutions with alanine for these 3 basic residues results in between 70 and 90% reduction of binding affinity of these synthetic peptides for this region of αVβ3. We have also determined that synthetic peptides with this structure (i.e., the region of vitronectin contains the following sequence $^{367}$KKQRFRHR$^{374}$ (SEQ ID NO:3) results in full stimulation of β3 phosphorylation, SHP-2 transfer to downstream signaling molecules and enhancement of activation of the IGF-I receptor in response to IGF-I. We have shown that synthetic peptides bearing this structure have full biologic activity and potentiate the effect of IGF-I on DNA synthesis, cell migration, and protein synthesis. Mutagenesis of the single arginine to alanine at position 374 in vitronectin results in not only a 70% decrease in binding, but also corresponding decreases in biologic activity as assessed by the three parameters noted above. Similarly alanine mutations of the first two basic residues also result in loss of biologic activity.

With respect to antagonists, we have determined that leaving the first two residues intact, that is leaving them both basic followed by addition of a hydrophobic residue at position 374 or a phosphorylated serine in position 374 results in competitive antagonist: that is these peptides retain some ability to bind to αVβ3 but do not activate β3 phosphorylation and/or SHP-2 transfer and do not enhance IGF-I stimulated receptor phosphorylation or cell division. An antagonist can also be prepared using sequences from other ligands that are known to bind to this β3 domain. For example if the heparin binding domain of IGFBP-5 (SEQ ID NO: 1) is used and there is a substitution for lysine 208 to alanine this peptide binds to β3 but inhibits IGF-I actions. These data are discussed in greater detail in Example 2 below.

More particular examples of agonist and antagonist active agents are given below.

Agonists. Agonists that may be used to carry out the present invention include but are not limited to compounds of Formula I:

(I)

(SEQ ID NO: 4)

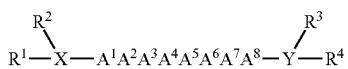

wherein:
$A^1$ is a basic amino acid or a phosphorylated serine;
$A^2$ is a basic amino acid;
$A^3$ is any amino acid;
$A^4$ is any amino acid;
$A^5$ is an aromatic amino acid;
$A^6$ is a basic amino acid;
$A^7$ is a basic amino acid;
$A^8$ is a basic amino acid or a phosphorylated serine;
X is a chain of 0-5 amino acids (any), inclusive, the N-terminal one of which is optionally bonded to $R^1$ and $R^2$;
Y is a chain of 0-4 amino acids, inclusive, the C-terminal one of which is optionally bonded to $R^3$ and $R^4$;
$R^1$, $R^2$, $R^3$, and $R^4$ are present or absent and are each independently selected from the group consisting of H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), and C7-C18 alkaryl (e.g., p-methylphenyl);
or a pharmaceutically acceptable salt thereof.

Antagonists. Antagonists that may be used to carry out the present invention include but are not limited to compounds of Formula II:

(II)

(SEQ ID NO: 5)

wherein:
$A^{11}$ is a basic amino acid;
$A^{12}$ is a basic amino acid;
$A^{13}$ is any amino acid;
$A^{14}$ is any amino acid;
$A^{15}$ is an aromatic amino acid;
$A^{16}$ is a basic amino acid;
$A^{17}$ is a basic amino acid;
$A^{18}$ is a noncharged or neutral amino acid or a hydrophobic amino acid;
X' is a chain of 0-5 amino acids (any), inclusive, the N-terminal one of which is optionally bonded to $R^{11}$ and $R^{12}$;
Y' is a chain of 0-4 amino acids, inclusive, the C-terminal one of which may be phosphoserine or may be optionally bonded to $R^{13}$ and $R^{14}$;
$R^{11}$, $R^{12}$, $R^{13}$, and $R^{14}$ are present or absent and are each independently selected from the group consisting of H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), and C7-C18 alkaryl (e.g., p-methylphenyl);
or a pharmaceutically acceptable salt thereof.

In Formulas I and II herein, the symbols X, Y, Z, $A^1$, $A^2$, $A^{12}$, and the like stand for an amino acid residue, i.e., =N—CH(R)—CO— when it is at the N-terminus, or —NH—CH(R)—CO—N= when it is at C-terminus, or —NH—CH(R)—CO— when it is not at the N- or C-terminus, where R denotes the side chain (or identifying group) of an amino acid or its residue. Also, when the amino acid residue is optically active, it is the L-form configuration that is intended unless the D-form is expressly designated.

Peptide agonists or antagonists of the present invention, such as compounds of Formula I and Formula II above, are preferably from 8 amino acids to 11, 14 or 20 amino acids in length, and may have a molecular weight of from 600, 800 or 900 up to about 1200 or 2000.

Making Peptides. Peptides of the present invention may be made in accordance with techniques known in the art. Using accepted techniques of chemical synthesis, the peptide may be built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide. Peptides of the present invention may also be produced through recombinant DNA procedures as are known in the art.

Pseudopeptide Bonds. In yet another aspect, the invention features analogs of Formula I or Formula II having at least one pseudopeptide bond between amino acid residues therein. By "pseudopeptide bond" it is meant that the carbon atom participating in the bond between two residues is reduced from a carbonyl carbon to a methylene carbon, i.e., $CH_2$—NH; or less preferably that of CO—NH is replaced with any of $CH_2$—S, $CH_2$—$CH_2$, $CH_2$—O, or $CH_2$—CO. Preferably, the pseudopeptide bonds are located between one or more amino acid residues. In addition, such pseudopeptide bond analogs can be used to form dimeric analogs as is described above. A detailed discussion of the chemistry of pseudopeptide bonds is given in Coy et al. (1988) *Tetrahedron* 44:835-841.

Analogs. Active agents include analogs of the compounds of Formula I and Formula II described herein. An "analog" is a chemical compound similar in structure to a first compound, and having either a similar or opposite physiologic action as the first compound. With particular reference to the present invention, analogs are those compounds which, while not having the amino acid sequences of the corresponding protein or peptide, are capable of acting as agonists or antagonists in substantially like manner to the active compounds described herein. Such analogs may be peptide or non-peptide analogs.

In protein or peptide molecules which interact with a receptor (specifically, the αVβ3 cysteine loop domain) the interaction between the protein or peptide and the receptor generally takes place at surface-accessible sites in a stable three-dimensional molecule. By arranging the critical binding site residues in an appropriate conformation, peptides analogs which mimic the essential surface features of the peptides described herein may be generated and synthesized in accordance with known techniques. Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science* 247, 28029 (1990); Rossmann, *Nature* 333, 392 (1988); Weis et al., *Nature* 333, 426 (1988); James et al., *Science* 260, 1937 (1993) (development of benzodiazepine peptidomimetic compounds based on the structure and function of tetrapeptide ligands).

Non-peptide mimetics of the agonists or antagonists of the present invention are also an aspect of this invention. Non-protein mimetics may be generated in accordance with known techniques such as using computer graphic modeling to design non-peptide, organic molecules able to agonize of antagonize binding in like manner as the active agents described herein. See, e.g., Knight, *BIO/Technology* 8, 105 (1990); Itzstein et al, *Nature* 363, 418 (1993) (peptidomimetic inhibitors of influenza virus enzyme, sialidase). Itzstein et al., *Nature* 363, 418 (1993), modeled the crystal structure of the sialidase receptor protein using data from x-ray crystallography studies and developed an inhibitor that would attach to active sites of the model; the use of nuclear magnetic resonance (NMR) data for modeling is also known in the art and such techniques may be utilized in carrying out the instant invention. See also Lam et al., *Science* 263, 380 (1994) regarding the rational design of bioavailable nonpeptide cyclic ureas that function as HIV protease inhibitors. Lam et al. used information from x-ray crystal structure studies of HIV protease inhibitor complexes to design nonpeptide inhibitors.

Hydrophilic Groups. Active agents of the present invention may include hydrophilic groups coupled thereto, particularly covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, peptide agonists or antagonists can be pegylated using a single 40,000 molecular weight polyethylene glycol moiety that is attached to the peptide.

Pharmaceutical Salts. The active compounds disclosed herein can, as noted above, be prepared and administered in the form of their pharmaceutically acceptable salts. Pharmaceutically acceptable salts are salts that retain the desired biological activity of the parent compound and do not impart excessive toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

C. Formulations and Administration

For administration in the methods of use described below, the active agent will generally be mixed, prior to administration, with a non-toxic, pharmaceutically acceptable carrier substance (e.g. normal saline or phosphate-buffered saline), and will be administered using any medically appropriate procedure, e.g., parenteral administration (e.g., injection) such as by intravenous or intra-arterial injection.

The active agents described above may be formulated for administration in a pharmaceutical carrier in accordance with known techniques. See, e.g., Remington, *The Science And*

*Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a liquid and is preferably formulated with the compound as a unit-dose formulation which may contain from 0.01 or 0.5% to 95% or 99% by weight of the active compound.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient.

The active agents may be administered by any medically appropriate procedure, e.g., normal intravenous or intra-arterial administration. In certain cases, direct administration to an atherosclerotic vessel may be desired.

Active agents may be provided in lyophilized form in a sterile aseptic container or may be provided in a pharmaceutical formulation in combination with a pharmaceutically acceptable carrier, such as sterile pyrogen-free water or sterile pyrogen-free physiological saline solution.

Dosage of the active agent for the methods of use described below will depend, among other things, the condition of the subject, the particular category or type of cancer being treated, the route of administration, the nature of the therapeutic agent employed, and the sensitivity of the tumor to the particular therapeutic agent. For example, the dosage will typically be about 1 to 10 micrograms per kilogram subject body weight. The specific dosage of the antibody is not critical, as long as it is effective to result in some beneficial effects in some individuals within an affected population. In general, the dosage may be as low as about 0.05, 0.1, 0.5, 1, 5, 10, 20 or 50 micrograms per kilogram subject body weight, or lower, and as high as about 5, 10, 20, 50, 75 or 100 micrograms per kilogram subject body weight, or even higher.

D. Methods of Use: Agonists

Agonist active agents of the present invention can be utilized for a variety of different diseases. One preferred target disease state would be children with short stature who secrete normal amounts of growth hormone. These are children who upon diagnostic testing cannot be proven to be growth hormone deficient but are short. There is a reasonable amount of evidence to show that they are relatively resistant to the actions of growth hormone and IGF-I. Therefore a factor that enhances IGF-I action should enhance the growth of these children and since their IGF-I secretion is intact, no other therapy should be required for growth optimization.

Another application is for subjects afflicted with defective retinal vascularization. Premature infants who are severely malnourished and do not synthesize adequate IGF-I particularly in the back of the retina. This results in delayed and maldeveloped vascularization of the retina which can result in blindness or extremely decreased visual acuity. There is a critical period between 26 and 29 weeks wherein IGF-I action is required. Although the cause of defective IGF-I action has not been firmly established, a factor which enhances IGF-I action on retinal vascular endothelial cells should provide a therapeutic benefit since these cells bear αVβ3 receptors.

Another application is to facilitate the development of collateral blood vessels following ischemic injury. Both peripheral vascular disease with claudication and myocardial infarction are associated with the development of collateral blood vessels during the healing period. The ability to form collaterals greatly determines the ability to recover from these ischemic insults. Although several factors such as vascular endothelial growth factor have been shown to enhance collateralization none has proven to be clinically efficacious in patients. A potential use of this compound would be to stimulate smooth muscle and endothelial cells during the process of collateral vessel development.

Another application involves the treatment or inhibition of neuronal atrophy and failure of neural process development. This applies specifically to degenerative dementias and to diabetic neuropathy.

Still another application is to treat hip fractures in the elderly. Infusion of high concentrations of IGF-I has been shown to accelerate healing from hip fractures in the elderly. The availability of this agent would enable to one to directly inject it with the fracture site with a peptide that is likely to enhance osteoblast activity in the presence of adequate IGF-I. The agonist can be administered with or without IGF-I to improve hip fracture healing.

Another application is to treat diabetic ischemic ulcers. In diabetic animal models, it has been shown that addition of IGF-I with one of its binding proteins to wounds results in improved wound healing. Since in diabetes IGF-I concentrations are low addition of this agonist with IGF-I to wounds is likely to result in better wound healing in the presence of diabetic ulcerations. In diabetic neuropathy it has been shown that neurons undergo rapid apoptosis and have poor axonal outgrowth unless adequate IGF-I is present. Since αVβ3 receptors are present on glial cells that provide support for neurons it is possible that this agonist could enhance neuronal outgrowth and the development of axonal processes and connections in diabetic neuropathy. In neurodegenerative diseases such as ALS and various dementias, IGF-I has been shown to inhibit neuronal apoptosis therefore therapy with this agent may be of some use in preventing these neurodegenerative conditions.

E. Methods of Use: Antagonists

Antagonism of IGF-I action has been shown to block lesion formation and early atherosclerotic lesion development. Administration of an antagonist that blocks this binding site on αVβ3 would antagonize the effect of matrix proteins that are abundant in atherosclerotic lesions such as vitronectin, osteopontin and fibrinogen. To the extent that heparin binding epidermal growth factor and connective tissue growth factor are active in atherosclerotic lesion development the antagonist would also act to inhibit their effects.

Another use of antagonists would be to treat inflammatory bowel disease. Intestinal smooth muscle cells express αVβ3 receptors and their proliferation in these diseases leads to intestinal strictures. Therefore inhibiting their growth with an antagonist could lead to prevention of this complication.

Another use of antagonists of the invention is in the treatment of osteoporosis. Osteoblasts do not express αVβ3 but it is expressed on osteoclasts which stimulate bone reabsorption. Therefore inhibition of stimulation of ligand occupancy on osteoclasts should result in enhancement of bone formation through the use of antagonist. Several proteins such as osteopontin are abundant in bone extracellular matrix and could be stimulating osteoclasts through this mechanism therefore antagonism of their action may allow IGF-I to increase bone formation without increasing bone resorption.

Another use of antagonists is to treat states of abnormal angiogenesis. Angiogenesis is important in tumor development but it is as important in other pathophysiologic processes such as diabetic retinopathy. Since endothelial cells express abundant αVβ3 receptors antagonists that inhibit the binding of endothelial growth factors such as vascular endothelial growth factor or heparin binding epidermal growth factor to αVβ3 through this heparin binding domain would be expected to lead to inhibition of angiogenesis therefore this antagonist is a useful drug in these clinical conditions.

Another use of antagonists is to treat cancers or tumors, particularly those that have αVβ3 receptors (e.g., Wilm's tumor, nephroblastoma, neuroblastoma). Although αVβ3 is not an abundant receptor on all tumor cells, several tumor cell types that express αVβ3 have been described. Approaches to date have generally targeted the RGD sequence in ligands that stimulate αVβ3 and used antagonists that are binding to this domain to inhibit αVβ3 actions. Our approach that is antagonizing the cysteine loop on αVβ3 provides a unique approach targeting this receptor as opposed to the RGD binding site and thus may have greater efficacy inhibiting the development of these tumors.

In the treatment of cancers or tumors the active agents of the present invention may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered concurrently. As used herein, the word "concurrently" means sufficiently close in time to produce a combined effect (that is, concurrently may be simultaneously, or it may be two or more administrations occurring before or after each other) As used herein, the phrase "radiation therapy" includes, but is not limited to, x-rays or gamma rays which are delivered from either an externally applied source such as a beam or by implantation of small radioactive sources. Examples of other suitable chemotherapeutic agents which may be concurrently administered with active agents as described herein include, but are not limited to, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine; Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. Nos. 6,537,988; 6,420,377). Such compounds may be given in accordance with techniques currently known for the administration thereof.

F. Antibodies

Antibodies and the production thereof are known. See, e.g., U.S. Pat. No. 6,849,719; see also U.S. Pat. Nos. 6,838,282; 6,835,817; 6,824,989.

Antibodies of the invention include antibodies that are modified, i.e., by the covalent attachment of any type of molecule to the antibody such that covalent attachment does not prevent the antibody from specifically binding to its binding site. For example, antibodies of the invention may be modified, e.g., by glycosylation, acetylation, pegylation, phosphorylation, amidation, or with other protecting/blocking groups, proteolytic cleavage, linkage to a cellular ligand or other protein, etc. Any of numerous chemical modifications may be carried out by known techniques, including but not limited to specific chemical cleavage, acetylation, formylation, metabolic synthesis of tunicamycin, etc. Additionally, the antibodies may contain one or more non-classical amino acids.

Polyclonal antibodies of the invention can be generated by any suitable method known in the art. For example, a suitable antigen can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum.*

Monoclonal antibodies can be prepared using a wide variety of techniques including the use of hybridoma, recombinant, and phage display technologies, or a combination thereof. For example, monoclonal antibodies can be produced using hybridoma techniques including those taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and known. Briefly, mice are immunized with an antigen or a cell expressing such antigen. Once an immune response is detected, e.g., antibodies specific for the antigen are detected in the mouse serum, the mouse spleen is harvested and splenocytes isolated. The splenocytes are then fused by known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain.

For example, antibodies can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include but are not limited to those disclosed in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art.

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and. a human immunoglobulin constant region. Methods for producing chimeric antibodies are known in the art. See e.g., Morrison, Science 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (see, e.g., U.S. Pat. Nos. 5,225,539; 5,530,101; and 5,585,089), veneering or resurfacing (see, e.g., EP 592,106; EP 519,596; Padlan, *Molecular Immunology* 28(4/5):489-498 (1991); Studnicka et al., *Protein Engineering* 7(6):805-814 (1994); Roguska et al., *PNAS* 91:969-973 (1994)), and chain shuffling (U.S. Pat. No. 5,565,332).

Completely human antibodies are desirable for therapeutic treatment, diagnosis, and/or detection of human patients. Human antibodies can be made by a variety of methods known in the art including phage display methods described above using antibody libraries derived from human immunoglobulin sequences. See, e.g., U.S. Pat. Nos. 4,444,887 and 4,716,111.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,413,923; 5,625,126; 5,633,425; 5,569,825; 5,661,016; 5,545,806; 5,814,318; and 5,939,598.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437-444; (1989) and Nissinoff, *J. Immunol.* 147(8):2429-2438 (1991)). For example antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The invention further provides polynucleotides comprising a nucleotide sequence encoding an antibody of the invention as described above. The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR. Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

G. Implants

Active compounds of the invention, particularly antagonists such as antibodies or peptides as described above, may be coupled to or conjugated to implants or implantable medical devices in accordance with known techniques for carrying out the methods described herein, or for combating problems associated with the implant such as stenosis and restenosis. See, e.g., U.S. Pat. Nos. 6,786,922; 6,746,686; 6,718,208; 6,617,142; 6,352,832; 6,238,872. Any implant can be so utilized, including but not limited to stents (e.g., vascular stents), electrodes, catheters, leads, implantable pacemaker or cardioverter housings, joints, screws, rods, ophthalmic implants (including, but not limited to, intraocular lens implants, glaucoma implants or drainage implants, and punctal implants or plugs), etc. The implants may be of any suitable material, including but not limited to organic polymers (including stable or inert polymers and biodegradable polymers), metals such as stainless steel and titanium, inorganic materials such as silicon, and composites thereof.

H. Screening Assays

The methods, storage media, data structures, and the like, along with compounds identified by such methods and methods of use thereof, may be implemented accordance with known techniques such as described in L. Tong et al., PCT Application WO 2004/063715, titled *Methods of Using Crystal Structure of Carboxyltransferase Domain of Acetyl-CoA Carboxylase, Modulators Thereof and Computer Methods.*

Advantageously the crystal structure of β3 integrin, including the cysteine loop domain thereof, is known, although not known for the purposes described herein.

Peterson et al Biochemistry 44:565, 2005 have utilized small angle light scattering, and in an earlier publication, NMR, to determine to the three dimensional structure of vitronectin. In their model the heparin binding domain is surface exposed and clearly distinct from the RGD binding domain as well as the plasminogen activator inhibitor-1 binding domain. Although the heparin binding domain is not cryptic they comment that polymerized vitronectin is likely to bind more avidly to heparin due to an even better exposure of this domain. Since multimeric forms of vitronectin occur in disease states such as atherosclerosis and in vitronectin that is associated with extracellular matrix, this may have pathophysiologic significance. Similarly the crystal structure of the extracellular portion of αVβ3 dimer with and without being complexed to RGD ligands has been reported (Science 294: 339, 2001 and Science 296:151, 2002). These two papers report the molecular coordinates of the cysteine loop structure between residues cysteine 177 and cysteine 184 hereafter termed the cysteine loop. This structure is mapped and the three dimensional structure is illustrated in FIG. 6 of the first manuscript. The paper clearly illustrates that this binding site is distinct from the RGD sequence binding site. It is described as a ligand specificity region but no further description of its functional properties are given in this publication. It is clear from the crystal structure that its surface is exposed. Similarly the active confirmation of the protein results in further surface exposure of this binding domain. The molecular coordinates are described and the GI extension #'s are 232004340 20664279 and 16975254. Similarly the extension numbers of the crystal structure are IL5GAZ-A5 and B0, B6, 7, 8, 9, 10 and C0, The Protein Data Bank (PDB) accession numbers for the unliganded and RGD liganded structures of αVβ3 integrin are 1JV2 and 1L5G, the disclosures of which are incorporated herein by reference in their entirety for their teachings. Tables 1 and 2 presented below provide the molecular coordinates for amino acid residues between cysteine 177 and cysteine 184 of the unliganded and RGD liganded structures of β3 integrin, respectively.

TABLE 1

Atomic coordinates for amino acid residues between cysteine 177 and cysteine 184 of β3 integrin

| CRYST1 | 130.000 | 130.000 | 307.300 | 90.00 | 90.00 120.00 P 32 2 1 | 6 |
|---|---|---|---|---|---|---|
| ORIGX1 | 1.000000 | 0.000000 | 0.000000 | 0.00000 | | |

TABLE 1-continued

Atomic coordinates for amino acid residues between cysteine 177 and cysteine 184 of β3 integrin

| | | | | | | | | | | |
|---|---|---|---|---|---|---|---|---|---|---|
| ORIGX2 | | 0.000000 | | 1.000000 | | 0.000000 | | 0.00000 | | |
| ORIGX3 | | 0.000000 | | 0.000000 | | 1.000000 | | 0.00000 | | |
| SCALE1 | | 0.007692 | | 0.004441 | | 0.000000 | | 0.00000 | | |
| SCALE2 | | 0.000000 | | 0.008882 | | 0.000000 | | 0.00000 | | |
| SCALE3 | | 0.000000 | | 0.000000 | | 0.003254 | | 0.00000 | | |
| ATOM | 8193 | N | CYS | B | 177 | 30.617 | 38.285 | 38.020 | 1.00 | 51.69 | N |
| ATOM | 8194 | CA | CYS | B | 177 | 29.881 | 38.955 | 39.076 | 1.00 | 61.73 | C |
| ATOM | 8195 | C | CYS | B | 177 | 30.997 | 39.840 | 39.641 | 1.00 | 63.92 | C |
| ATOM | 8196 | O | CYS | B | 177 | 31.309 | 39.784 | 40.819 | 1.00 | 67.08 | O |
| ATOM | 8197 | CB | CYS | B | 177 | 29.473 | 37.927 | 40.157 | 1.00 | 67.19 | C |
| ATOM | 8198 | SG | CYS | B | 177 | 28.097 | 36.748 | 39.847 | 1.00 | 89.98 | S |
| ATOM | 8199 | N | TYR | B | 178 | 31.638 | 40.596 | 38.756 | 1.00 | 64.48 | N |
| ATOM | 8200 | CA | TYR | B | 178 | 32.764 | 41.495 | 39.061 | 1.00 | 64.75 | C |
| ATOM | 8201 | C | TYR | B | 178 | 32.786 | 42.370 | 40.337 | 1.00 | 64.07 | C |
| ATOM | 8202 | O | TYR | B | 178 | 33.761 | 42.313 | 41.085 | 1.00 | 62.11 | O |
| ATOM | 8203 | CB | TYR | B | 178 | 33.022 | 42.386 | 37.846 | 1.00 | 74.79 | C |
| ATOM | 8204 | CG | TYR | B | 178 | 31.983 | 43.478 | 37.675 | 1.00 | 89.90 | C |
| ATOM | 8205 | CD1 | TYR | B | 178 | 30.617 | 43.197 | 37.784 | 1.00 | 100.00 | C |
| ATOM | 8206 | CD2 | TYR | B | 178 | 32.364 | 44.805 | 37.472 | 1.00 | 97.33 | C |
| ATOM | 8207 | CE1 | TYR | B | 178 | 29.656 | 44.214 | 37.704 | 1.00 | 100.00 | C |
| ATOM | 8208 | CE2 | TYR | B | 178 | 31.409 | 45.833 | 37.391 | 1.00 | 100.00 | C |
| ATOM | 8209 | CZ | TYR | B | 178 | 30.058 | 45.528 | 37.508 | 1.00 | 100.00 | C |
| ATOM | 8210 | OH | TYR | B | 178 | 29.105 | 46.526 | 37.450 | 1.00 | 99.70 | O |
| ATOM | 8211 | N | ASP | B | 179 | 31.761 | 43.212 | 40.540 | 1.00 | 61.63 | N |
| ATOM | 8212 | CA | ASP | B | 179 | 31.664 | 44.120 | 41.705 | 1.00 | 62.19 | C |
| ATOM | 8213 | C | ASP | B | 179 | 32.085 | 43.413 | 42.972 | 1.00 | 68.31 | C |
| ATOM | 8214 | O | ASP | B | 179 | 33.148 | 43.669 | 43.539 | 1.00 | 70.06 | O |
| ATOM | 8215 | CB | ASP | B | 179 | 30.224 | 44.597 | 41.919 | 1.00 | 60.12 | C |
| ATOM | 8216 | CG | ASP | B | 179 | 29.704 | 45.424 | 40.782 | 1.00 | 66.56 | C |
| ATOM | 8217 | OD1 | ASP | B | 179 | 28.590 | 45.129 | 40.294 | 1.00 | 60.98 | O |
| ATOM | 8218 | OD2 | ASP | B | 179 | 30.399 | 46.381 | 40.386 | 1.00 | 80.12 | O |
| ATOM | 8219 | N | MET | B | 180 | 31.209 | 42.519 | 43.415 | 1.00 | 79.09 | N |
| ATOM | 8220 | CA | MET | B | 180 | 31.470 | 41.708 | 44.591 | 1.00 | 88.86 | C |
| ATOM | 8221 | C | MET | B | 180 | 32.586 | 40.865 | 43.984 | 1.00 | 90.63 | C |
| ATOM | 8222 | O | MET | B | 180 | 32.520 | 40.553 | 42.794 | 1.00 | 92.27 | O |
| ATOM | 8223 | CB | MET | B | 180 | 30.219 | 40.863 | 44.929 | 1.00 | 98.30 | C |
| ATOM | 8224 | CG | MET | B | 180 | 29.616 | 40.019 | 43.759 | 1.00 | 100.00 | C |
| ATOM | 8225 | SD | MET | B | 180 | 27.803 | 40.099 | 43.408 | 1.00 | 91.76 | S |
| ATOM | 8226 | CE | MET | B | 180 | 27.856 | 41.139 | 41.950 | 1.00 | 88.30 | C |
| ATOM | 8227 | N | LYS | B | 181 | 33.663 | 40.604 | 44.724 | 1.00 | 89.72 | N |
| ATOM | 8228 | CA | LYS | B | 181 | 34.763 | 39.829 | 44.143 | 1.00 | 93.91 | C |
| ATOM | 8229 | C | LYS | B | 181 | 34.430 | 38.380 | 43.748 | 1.00 | 93.74 | C |
| ATOM | 8230 | O | LYS | B | 181 | 35.074 | 37.810 | 42.857 | 1.00 | 94.02 | O |
| ATOM | 8231 | CB | LYS | B | 181 | 36.004 | 39.857 | 45.047 | 1.00 | 98.76 | C |
| ATOM | 8232 | CG | LYS | B | 181 | 37.208 | 39.133 | 44.442 | 1.00 | 100.00 | C |
| ATOM | 8233 | CD | LYS | B | 181 | 38.370 | 39.089 | 45.410 | 1.00 | 100.00 | C |
| ATOM | 8234 | CE | LYS | B | 181 | 39.471 | 38.167 | 44.899 | 1.00 | 100.00 | C |
| ATOM | 8235 | NZ | LYS | B | 181 | 40.690 | 38.200 | 45.762 | 1.00 | 100.00 | N |
| ATOM | 8236 | N | THR | B | 182 | 33.382 | 37.836 | 44.360 | 1.00 | 92.50 | N |
| ATOM | 8237 | CA | THR | B | 182 | 32.941 | 36.458 | 44.122 | 1.00 | 95.53 | C |
| ATOM | 8238 | C | THR | B | 182 | 32.590 | 36.101 | 42.662 | 1.00 | 94.42 | C |
| ATOM | 8239 | O | THR | B | 182 | 31.417 | 36.137 | 42.272 | 1.00 | 100.00 | O |
| ATOM | 8240 | CB | THR | B | 182 | 31.723 | 36.138 | 45.009 | 1.00 | 99.31 | C |
| ATOM | 8241 | OG1 | THR | B | 182 | 31.913 | 36.732 | 46.313 | 1.00 | 100.00 | O |
| ATOM | 8242 | CG2 | THR | B | 182 | 31.526 | 34.632 | 45.150 | 1.00 | 99.19 | C |
| ATOM | 8243 | N | THR | B | 183 | 33.584 | 35.681 | 41.879 | 1.00 | 92.69 | N |
| ATOM | 8244 | CA | THR | B | 183 | 33.346 | 35.309 | 40.483 | 1.00 | 88.83 | C |
| ATOM | 8245 | C | THR | B | 183 | 32.313 | 34.189 | 40.349 | 1.00 | 83.16 | C |
| ATOM | 8246 | O | THR | B | 183 | 32.163 | 33.327 | 41.224 | 1.00 | 81.19 | O |
| ATOM | 8247 | CB | THR | B | 183 | 34.653 | 34.915 | 39.734 | 1.00 | 87.66 | C |
| ATOM | 8248 | OG1 | THR | B | 183 | 35.311 | 33.836 | 40.416 | 1.00 | 93.17 | O |
| ATOM | 8249 | CG2 | THR | B | 183 | 35.597 | 36.121 | 39.631 | 1.00 | 90.15 | C |
| ATOM | 8250 | N | CYS | B | 184 | 31.593 | 34.226 | 39.236 | 1.00 | 78.27 | N |
| ATOM | 8251 | CA | CYS | B | 184 | 30.543 | 33.265 | 38.955 | 1.00 | 71.84 | C |
| ATOM | 8252 | C | CYS | B | 184 | 30.528 | 32.977 | 37.459 | 1.00 | 68.43 | C |
| ATOM | 8253 | O | CYS | B | 184 | 31.391 | 33.445 | 36.719 | 1.00 | 68.40 | O |
| ATOM | 8254 | CB | CYS | B | 184 | 29.193 | 33.867 | 39.372 | 1.00 | 78.22 | C |
| ATOM | 8255 | SG | CYS | B | 184 | 28.756 | 35.396 | 38.458 | 1.00 | 81.45 | S |

TABLE 2

Atomic coordinates for amino acid residues between cysteine 177 and cysteine 184 of β3 integrin complexed with an Arg-Gly-Asp (RGD) ligand

| | | | | | | | | | | |
|---|---|---|---|---|---|---|---|---|---|---|
| CRYST1 | 129.790 | 129.790 | 308.780 | 90.00 | 90.00 | 120.00 | P 32 2 1 | | 6 | |
| ORIGX1 | 1.000000 | 0.000000 | 0.000000 | | 0.00000 | | | | | |
| ORIGX2 | 0.000000 | 1.000000 | 0.000000 | | 0.00000 | | | | | |
| ORIGX3 | 0.000000 | 0.000000 | 1.000000 | | 0.00000 | | | | | |
| SCALE1 | 0.007705 | 0.004448 | 0.000000 | | 0.00000 | | | | | |
| SCALE2 | 0.000000 | 0.008897 | 0.000000 | | 0.00000 | | | | | |
| SCALE3 | 0.000000 | 0.000000 | 0.003239 | | 0.00000 | | | | | |
| ATOM | 8193 | N | CYS | B | 177 | 29.514 | 39.700 | 37.901 | 1.00 | 39.17 | N |
| ATOM | 8194 | CA | CYS | B | 177 | 29.723 | 40.091 | 39.299 | 1.00 | 49.86 | C |
| ATOM | 8195 | C | CYS | B | 177 | 31.188 | 40.306 | 39.619 | 1.00 | 51.72 | C |
| ATOM | 8196 | O | CYS | B | 177 | 31.741 | 39.770 | 40.581 | 1.00 | 52.27 | O |
| ATOM | 8197 | CB | CYS | B | 177 | 29.045 | 39.124 | 40.271 | 1.00 | 48.58 | C |
| ATOM | 8198 | SG | CYS | B | 177 | 29.786 | 37.472 | 40.399 | 1.00 | 47.78 | S |
| ATOM | 8199 | N | TYR | B | 178 | 31.806 | 41.091 | 38.742 | 1.00 | 55.89 | N |
| ATOM | 8200 | CA | TYR | B | 178 | 33.192 | 41.474 | 38.835 | 1.00 | 56.91 | C |
| ATOM | 8201 | C | TYR | B | 178 | 33.247 | 42.935 | 39.269 | 1.00 | 55.86 | C |
| ATOM | 8202 | O | TYR | B | 178 | 34.278 | 43.428 | 39.698 | 1.00 | 55.78 | O |
| ATOM | 8203 | CB | TYR | B | 178 | 33.886 | 41.150 | 37.519 | 1.00 | 60.90 | C |
| ATOM | 8204 | CG | TYR | B | 178 | 34.649 | 42.246 | 36.813 | 1.00 | 70.75 | C |
| ATOM | 8205 | CD1 | TYR | B | 178 | 34.050 | 43.464 | 36.482 | 1.00 | 72.46 | C |
| ATOM | 8206 | CD2 | TYR | B | 178 | 35.952 | 42.013 | 36.363 | 1.00 | 82.19 | C |
| ATOM | 8207 | CE1 | TYR | B | 178 | 34.732 | 44.415 | 35.712 | 1.00 | 85.76 | C |
| ATOM | 8208 | CE2 | TYR | B | 178 | 36.638 | 42.943 | 35.596 | 1.00 | 86.77 | C |
| ATOM | 8209 | CZ | TYR | B | 178 | 36.026 | 44.137 | 35.270 | 1.00 | 89.20 | C |
| ATOM | 8210 | OH | TYR | B | 178 | 36.707 | 45.026 | 34.463 | 1.00 | 91.89 | O |
| ATOM | 8211 | N | ASP | B | 179 | 32.110 | 43.616 | 39.165 | 1.00 | 58.12 | N |
| ATOM | 8212 | CA | ASP | B | 179 | 31.996 | 44.992 | 39.625 | 1.00 | 62.70 | C |
| ATOM | 8213 | C | ASP | B | 179 | 31.630 | 44.883 | 41.112 | 1.00 | 64.92 | C |
| ATOM | 8214 | O | ASP | B | 179 | 30.827 | 45.659 | 41.645 | 1.00 | 62.59 | O |
| ATOM | 8215 | CB | ASP | B | 179 | 30.929 | 45.780 | 38.833 | 1.00 | 63.77 | C |
| ATOM | 8216 | CG | ASP | B | 179 | 29.536 | 45.155 | 38.899 | 1.00 | 67.28 | C |
| ATOM | 8217 | OD1 | ASP | B | 179 | 29.164 | 44.447 | 37.938 | 1.00 | 73.03 | O |
| ATOM | 8218 | OD2 | ASP | B | 179 | 28.800 | 45.397 | 39.886 | 1.00 | 59.16 | O |
| ATOM | 8219 | N | MET | B | 180 | 32.200 | 43.857 | 41.747 | 1.00 | 66.78 | N |
| ATOM | 8220 | CA | MET | B | 180 | 32.010 | 43.546 | 43.162 | 1.00 | 74.44 | C |
| ATOM | 8221 | C | MET | B | 180 | 33.018 | 42.463 | 43.546 | 1.00 | 75.25 | C |
| ATOM | 8222 | O | MET | B | 180 | 33.614 | 42.506 | 44.625 | 1.00 | 79.74 | O |
| ATOM | 8223 | CB | MET | B | 180 | 30.585 | 43.043 | 43.437 | 1.00 | 74.85 | C |
| ATOM | 8224 | CG | MET | B | 180 | 30.158 | 41.826 | 42.616 | 1.00 | 72.71 | C |
| ATOM | 8225 | SD | MET | B | 180 | 28.776 | 40.893 | 43.337 | 1.00 | 69.56 | S |
| ATOM | 8226 | CE | MET | B | 180 | 27.571 | 42.205 | 43.619 | 1.00 | 71.52 | C |
| ATOM | 8227 | N | LYS | B | 181 | 33.189 | 41.504 | 42.633 | 1.00 | 76.92 | N |
| ATOM | 8228 | CA | LYS | B | 181 | 34.102 | 40.354 | 42.748 | 1.00 | 77.50 | C |
| ATOM | 8229 | C | LYS | B | 181 | 33.709 | 39.072 | 43.481 | 1.00 | 72.04 | C |
| ATOM | 8230 | O | LYS | B | 181 | 33.668 | 39.012 | 44.714 | 1.00 | 72.51 | O |
| ATOM | 8231 | CB | LYS | B | 181 | 35.525 | 40.773 | 43.147 | 1.00 | 79.56 | C |
| ATOM | 8232 | CG | LYS | B | 181 | 36.399 | 41.191 | 41.967 | 1.00 | 80.77 | C |
| ATOM | 8233 | CD | LYS | B | 181 | 35.869 | 40.672 | 40.615 | 1.00 | 81.67 | C |
| ATOM | 8234 | CE | LYS | B | 181 | 35.834 | 39.138 | 40.467 | 1.00 | 85.27 | C |
| ATOM | 8235 | NZ | LYS | B | 181 | 34.951 | 38.704 | 39.323 | 1.00 | 80.43 | N |
| ATOM | 8236 | N | THR | B | 182 | 33.503 | 38.032 | 42.678 | 1.00 | 63.31 | N |
| ATOM | 8237 | CA | THR | B | 182 | 33.138 | 36.694 | 43.133 | 1.00 | 63.32 | C |
| ATOM | 8238 | C | THR | B | 182 | 33.327 | 35.778 | 41.921 | 1.00 | 62.57 | C |
| ATOM | 8239 | O | THR | B | 182 | 33.167 | 34.561 | 42.003 | 1.00 | 67.53 | O |
| ATOM | 8240 | CB | THR | B | 182 | 31.670 | 36.635 | 43.650 | 1.00 | 64.03 | C |
| ATOM | 8241 | OG1 | THR | B | 182 | 31.565 | 37.379 | 44.873 | 1.00 | 70.53 | O |
| ATOM | 8242 | CG2 | THR | B | 182 | 31.225 | 35.189 | 43.915 | 1.00 | 61.10 | C |
| ATOM | 8243 | N | THR | B | 183 | 33.718 | 36.385 | 40.805 | 1.00 | 59.72 | N |
| ATOM | 8244 | CA | THR | B | 183 | 33.960 | 35.682 | 39.549 | 1.00 | 60.67 | C |
| ATOM | 8245 | C | THR | B | 183 | 32.872 | 34.710 | 39.065 | 1.00 | 56.82 | C |
| ATOM | 8246 | O | THR | B | 183 | 33.177 | 33.743 | 38.357 | 1.00 | 59.75 | O |
| ATOM | 8247 | CB | THR | B | 183 | 35.333 | 34.960 | 39.557 | 1.00 | 58.54 | C |
| ATOM | 8248 | OG1 | THR | B | 183 | 35.680 | 34.597 | 40.895 | 1.00 | 53.98 | O |
| ATOM | 8249 | CG2 | THR | B | 183 | 36.419 | 35.845 | 38.966 | 1.00 | 61.78 | C |
| ATOM | 8250 | N | CYS | B | 184 | 31.612 | 34.971 | 39.424 | 1.00 | 52.33 | N |
| ATOM | 8251 | CA | CYS | B | 184 | 30.493 | 34.121 | 38.998 | 1.00 | 43.94 | C |
| ATOM | 8252 | C | CYS | B | 184 | 30.506 | 34.081 | 37.486 | 1.00 | 38.56 | C |
| ATOM | 8253 | O | CYS | B | 184 | 30.486 | 35.116 | 36.837 | 1.00 | 35.49 | O |
| ATOM | 8254 | CB | CYS | B | 184 | 29.161 | 34.704 | 39.457 | 1.00 | 46.67 | C |
| ATOM | 8255 | SG | CYS | B | 184 | 28.929 | 36.411 | 38.895 | 1.00 | 44.19 | S |

In general any method known to those skilled in the art may be used to process X-ray diffraction data. In addition, in order to determine the atomic structure of a β3 integrin according to the present invention, multiple isomorphous replacement (MIR) analysis, model building and refinement may be performed. For MIR analysis, the crystals may be soaked in heavy-atoms to produce heavy atom derivatives necessary for MIR analysis. As used herein, heavy atom derivative or derivatization refers to the method of producing a chemically modified form of a protein or protein complex crystal wherein said protein is specifically bound to a heavy atom within the crystal. In practice a crystal is soaked in a solution containing heavy metal atoms or salts, or organometallic compounds, e.g., lead chloride, gold cyanide, thimerosal, lead acetate, uranyl acetate, mercury chloride, gold chloride, etc., which can diffuse through the crystal and bind specifically to the protein. The location(s) of the bound heavy metal atom(s) or salts can be determined by X-ray diffraction analysis of the soaked crystal. This information is used to generate MIR phase information which is used to construct the three-dimensional structure of the crystallized cysteine loop domain of a β3 integrin. Thereafter, an initial model of the three-dimensional structure may be built using the program 0 (Jones et al., 1991, *Acta Crystallogr. A*47:110-119). The interpretation and building of the structure may be further facilitated by use of the program CNS (Brunger et al., 1998, *Acta Crystallogr. D*54:905-921).

The method of molecular replacement broadly refers to a method that involves generating a preliminary model of the three-dimensional structure of crystal of a cysteine loop structure of a β3 integrin of the present invention. Molecular replacement is achieved by orienting and positioning a molecule whose structural coordinates are known within the unit cell as defined by the X-ray diffraction pattern obtained from the cysteine loop domain of a β3 integrin under study (or the corresponding enzyme/substrate complex or enzyme/inhibitor complex) so as to best account for the observed diffraction pattern of the unknown crystal. Phases can then be calculated from this model and combined with the observed amplitudes to give an approximate Fourier synthesis of the structure. This in turn can be subject to any of several forms of refinement to provide a final, accurate structure. The molecular replacement method may be applied using techniques known to the skilled artisan.

The three-dimensional structures and the specific atomic coordinates associated with said structures of the cysteine loop domain of β3, alone or in complex with a substrate or specific binding ligand such as heparin, are useful for solving the structure of crystallized forms of heparin binding domains of other β3 ligands. Such proteins comprise a root mean square deviation (RMSD) of no greater than 2.0 Å, 1.5 Å, 1.0 Å or 0.5 Å in the positions of Cα atoms for at least 50 percent or more of the amino acids of the structure of the cysteine loop domain of the β3 integrin. Such an RMSD may be expected based on the amino acid sequence identity. Chothia and Lesk, 1986, *EMBO J.* 5:823-826.

Modulators of a β3 integrin, and hence of IGF-1 activity, can be designed using three-dimensional structures obtained as set forth in the preceding section and the Examples section below. These structures may be used to design or screen for molecules that are able to form the desired interactions with one or more binding sites of the cysteine loop domain.

The models of the cysteine loop domain (and sub-regions, including active sites, binding sites or cavities thereof) of a β3 integrin described herein may be used to either directly develop a modulator for a β3 integrin. The ability for such a modulator to modulate the activity of a cysteine loop domain of a β3 integrin can be confirmed by further computer analysis, and/or by in vitro and/or in vivo testing.

A model of a cysteine loop domain may be comprised in a virtual or actual protein structure that is smaller than, larger than, or the same size as a native cysteine loop domain of a β3 integrin protein. The protein environment surrounding the active site model may be homologous or identical to the native cysteine loop domain of a β3 integrin, or it may be partially or completely non-homologous.

Thus, the present invention provides for a method for rationally designing a modulator of a β3 integrin, comprising the steps of (i) producing a computer readable model of a molecule comprising a region (i.e., an active site, reactive site, or a binding site) of a cysteine loop domain of β3 integrin (e.g. human or pig β3 integrin); and (ii) using the model to design a test compound having a structure and a charge distribution compatible with (i.e. able to be accommodated within) the region of the cysteine loop domain, wherein the test compound can comprise a functional group that may interact with the active site to modulate activity. If the crystal structure is not available for the cysteine loop domain to be examined, homology modeling methods known to those of ordinary skill in the art may be used to produce a model, which then may be used to design test compounds as described above.

The atomic coordinates of atoms of the cysteine loop domain (or a region/portion thereof) of a β3 integrin or a β3 integrin-related enzyme may be used in conjunction with computer modeling using a docking program such as GRAM, DOCK, HOOK or AUTODOCK (Dunbrack et al., 1997, *Folding & Design* 2:27-42) to identify potential modulators. This procedure can include computer fitting of potential modulators to a model of a cysteine loop domain (including models of regions of a cysteine loop domain, for example, an active site, or a binding site) to ascertain how well the shape and the chemical structure of the potential modulator will complement the active site or to compare the potential modulators with the binding of substrate or known inhibitor molecules in the active site.

Computer programs may be employed to estimate the attraction, repulsion and/or steric hindrance associated with a postulated interaction between the reactive site model and the potential modulator compound. Generally, characteristics of an interaction that are associated with modulator activity include, but are not limited to, tight fit, low steric hindrance, positive attractive forces, and specificity.

Modulator compounds of the present invention may also be designed by visually inspecting the three-dimensional structure of a reactive site of the cysteine loop domain of a β3 integrin, a technique known in the art as "manual" drug design. Manual drug design may employ visual inspection and analysis using a graphics visualization program known in the art.

As an alternative or an adjunct to rationally designing modulators, random screening of a small molecule library, a peptide library or a phage library for compounds that interact with and/or bind to a site/region of interest (i.e., a binding site, active site or a reactive site, for example) of the cysteine loop domain of a β3 integrin may be used to identify useful compounds. Such screening may be virtual;

small molecule databases can be computationally screened for chemical entities or compounds that can bind to or otherwise interact with a virtual model of an active site, binding site or reactive site of a cysteine loop domain of a β3 integrin. Alternatively, screening can be against actual molecular models of the cysteine loop domain or portions thereof. Further, antibodies can be generated that bind to a site of interest of the cysteine loop domain of β3. After candidate (or "test") compounds that can bind to the cysteine loop domain are identified, the compounds can then be tested to determine whether they can modulate cysteine loop domain activity (see below).

In one embodiment, β3 integrins containing cysteine loop domains, nucleic acids, and cells containing and/or expressing the cysteine loop domains are used in screening assays. Screens may be designed to first find candidate compounds that can bind to a cysteine loop domain or portion thereof, and then these compounds may be used in assays that evaluate the ability of the candidate compound to modulate the cysteine loop domain or β3 integrin activity. Thus, as will be appreciated by those in the art, there are a number of different assays which may be run, including binding assays and activity assays. In one aspect, candidate compounds are first tested to determine whether they can bind to a particular binding site of the heparin binding domain.

Thus, in one embodiment, the methods comprise combining a cysteine loop domain or portion thereof and a candidate compound, and determining the binding of the candidate compound to the cysteine loop domain or portion thereof. In some embodiments of the methods herein, the cysteine loop domain (or portion thereof) or the candidate agent is non-diffusably bound to an insoluble support having isolated sample receiving areas (e.g., a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples—i.e., they enable high-throughput screening. Following binding of the cysteine loop domain, excess unbound material is removed by washing. The sample receiving areas may then be blocked through incubation with bovine serum albumin (BSA), caseine or other innocuous protein or other moiety.

A candidate compound is added to the assay. Candidate compounds include, but are not limited to, specific antibodies, compounds from chemical libraries, peptide analogs, etc. Of particular interest are screening assays for compounds that have a low toxicity for human cells. A wide variety of assays may be used for this purpose, including labeled in vitro protein-protein binding assays, immunoassays for protein binding, NMR assays to determine protein-protein or protein-chemical compound binding, and the like. Candidate compounds can also include insecticides, herbicides or fungicides.

The term "candidate compound" as used herein describes any molecule, e.g., protein, oligopeptide, small organic molecule, polysaccharide, polynucleotide, etc., with the capability of directly or indirectly modulating heparin binding domain or β3 integrin activity. Generally a plurality of assay mixtures are run in parallel with different compound concentrations to obtain a differential response to the various concentrations. Typically, one of these concentrations serves as a negative control, i.e., at zero concentration or below the level of detection.

Candidate compounds can encompass numerous chemical classes, though typically they are organic molecules, and in one embodiment they are small organic compounds having a molecular weight of more than 100 and less than about 2,500 daltons. Candidate compounds can comprise functional groups necessary for structural interaction with proteins, for example hydrogen bonding, and typically include at least an amine, carbonyl, hydroxyl or carboxyl group, preferably at least two of the functional chemical groups. The candidate compounds can comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate compounds can be obtained from a wide variety of sources including libraries of synthetic or natural compounds. For example, numerous means are available for random and directed synthesis of a wide variety of organic compounds and biomolecules, including combinatorial chemical synthesis and the expression of randomized peptides or oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. In one embodiment, the library is fully randomized, with no sequence preferences or constants at any position. In another, the library is biased. That is, some positions within the sequence are either held constant, or are selected from a limited number of possibilities.

The determination of the binding of the candidate compound to the cysteine loop domain may be done in a number of ways. In one embodiment, the candidate compound is labeled, and binding determined directly. For example, this may be done by attaching all or a portion of the cysteine loop domain to a solid support, adding a labeled candidate compound (for example a fluorescent label or radioactive label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g., radioisotope, fluorescers, enzyme, antibodies, particles such as magnetic particles, chemiluminescers, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal.

In one embodiment, the binding of the candidate compound is determined through the use of competitive binding assays. In this embodiment, the competitor is a binding moiety known to bind to the cysteine loop domain, such as an antibody, peptide, ligand, etc. Under certain circumstances, there may be competitive binding as between the candidate compound and the known binding moiety, with the binding moiety displacing the bioactive agent.

In one embodiment, the candidate compound is labeled. Either the candidate compound, or the competitor, or both, is added first to the cysteine loop domain for a time sufficient to allow binding, if present. Incubations may be performed at any temperature which facilitates optimal binding, typically between 4 and 40° C. Incubation periods are selected for optimum binding but may also be optimized to facilitate rapid high-throughput screening. Typically between 0.1 and 1 hour will be sufficient. Excess reagent is generally removed or washed away. The second component is then added, and the presence or absence of the labeled component is followed, to indicate binding.

In one embodiment, the competitor is added first, followed by the candidate compound. Displacement of the competitor is an indication that the candidate compound is binding to the cysteine loop domain and thus is capable of binding to, and potentially modulating, the activity of the cysteine loop domain. In this embodiment, either component can be labeled. Thus, for example, if the competitor is labeled, the presence of label in the wash solution indicates displacement of the competitor by the candidate compound. Alternatively, if the candidate compound is labeled, the presence of the label on the support indicates displacement of the candidate compound.

In one embodiment, a potential ligand for a cysteine loop domain can be obtained by screening a recombinant bacteriophage library (Scott and Smith, *Science,* 249:386-390 (1990); Cwirla et al., *Proc. Natl. Acad. Sci.,* 87:6378-6382 (1990); Devlin et al., *Science,* 249:404-406 (1990). Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive heparin binding domain (or portion thereof). After a specified incubation period, the filters can be thoroughly washed and developed for autoradiography. Plaques containing the phage that bind to the radioactive heparin binding domain or portion thereof can then be identified. These phages can be further cloned and then retested for their ability to bind to the cysteine loop domain as before. Once the phages have been purified, the binding sequence contained within the phage can be determined by standard DNA sequencing techniques. Once the DNA sequence is known, synthetic peptides can be generated which represents these sequences, and further binding studies can be performed as discussed herein.

In another embodiment, a potential ligand for a cysteine loop domain can be obtained by screening candidate compounds by NMR (see for example, U.S. Patent Application Publication No. US2003/0148297A1 or Pellecchia et al., *Nature Reviews Drug Discovery,* 1:211-219 (2002)). As mentioned, a cysteine loop domain or portions thereof can be immobilized to all types of solid supports. It is not needed that the binding be a covalent binding. It is only required that the target is kept immobilized in the NMR measuring environment. Moreover, the immobilization need not be directly to the solid support; it may also occur indirectly through suitable bridging moieties or molecules, or through spacers. Very suitable supports are solid polymers used in chromatography, such as polystyrene, sepharose and agarose resins and gels, e.g. in bead form or in a porous matrix form. Additionally, appropriately chemically modified silicon based materials are also very suitable supports.

Any soluble molecule can be used as a compound that is a candidate to binding to the cysteine loop domain. It is not necessary that the said soluble molecule is water-soluble. Any liquid medium that does not denature the said compound nor the cysteine loop domain molecule can be used in the NMR measurements. The cysteine loop domain target molecule is immobilized to a suitable support, such as a solid resin, and additionally placed in a suitable NMR probe, for example, a flow injection NMR probe, for the duration of the screening. Each sample of the compounds to be screened, e.g. the compounds from a library, is then applied to the immobilized target by pumping it through, along or via the solid support. The sample to be assayed may contain a single component suspected of binding to the cysteine loop domain target molecule, or may contain multiple components of a compound library or other type of collection or mixture. The flow may be stopped when a desired level of concentration of the compounds to be assayed is reached in the target containing probe or vessel.

For the acquisition of the NMR spectra, in principle any NMR pulse sequence capable of detecting resonances from dissolved molecule samples and, preferably suppressing residual solvent signals, such as by pulsed field gradients, may be used to detect binding. In practice, however, a one-dimensional $^1$H-NMR spectrum is acquired with sufficient resolution and sensitivity to detect and quantitate resonances derived from each compound being assayed in the presence of the control solid support. In addition, a second spectrum recorded using the same NMR protocol, is acquired for the same solution of screenable compounds in the presence of the solid support containing the immobilized cysteine loop domain target molecule. Optionally, a third spectrum may be acquired in the presence of the solid support containing the immobilized cysteine loop domain target molecule in order to detect extremely weak target binding. This spectrum can be recorded while using a diffusion or T2 filter.

After acquisition of the NMR spectrum, the sample of small compound or compounds is washed out of the NMR probe containing the target immobilized solid support. Subsequently, the next sample can be applied to the probe in a stopped-flow manner. Throughout the entire screening process a single sample of the target immobilized solid support remains in the NMR probe. The target immobilized solid support need only be changed should the target become denatured, chemically degraded or saturated by a tight-binding compound that cannot be washed away. In order to safeguard that certain compounds do not bind in such a way that the target molecule is blocked, at certain stages, a control is carried out to check the availability of binding opportunities to the target molecule.

The NMR spectra are preferably compared by subtracting one of the two NMR data sets from the other, thereby creating a difference spectrum. In general, since the target molecule is essentially in the solid phase, the resonances from compounds that bind to the target molecule are broadened beyond detection while in the bound state. Thus, binding is sensitively and reliably detectable by a decrease in height of peaks that derive exclusively from the solution form of compounds binding to the target molecule. This effect is most easily seen in the difference spectra. An alternative approach that can be used to quantitate the affinity of the target-ligand interaction is to determine peak areas (e.g. by integrating) in the control and experimental spectra and compare the values of these areas. Although it is possible to carry out the NMR screening method in batch mode, in the flow-injection set-up, one sample of target may be used to screen an entire library.

Biological or Biochemical Screening Assays. Compounds can additionally be screened for activity in modulating cellular activation by IGF-1 in bioassays or chemical assays of the present invention. Compounds identified as modulators or potential modulators of IGF-1 activity by methods as described above may be further screened for specific activity as agonists or antagonists in in vivo or in vitro assays in accordance with known techniques, and/or as discussed further below.

Assay Methodologies

Methods to assess biochemical and biological activity of enhancers or inhibitors of αVβ3.

Modification of IGF-I actions. In addition to competitive binding assays, in order to determine whether compounds that bind to the cysteine loop binding site on αVβ3 influence IGF-I signaling and actions it has necessitated the utilization of assays that assess the biochemical and biologic actions that are stimulated when this site is activated by ligands and how this alters the cellular responses to IGF-I. Inhibitors will obviously inhibit the ability of IGF-I to stimulate these cellular processes whereas stimulators will facilitate its ability to do so. These assays include but are not totally limited to the following: β3 subunit phosphorylation, β3 binding to SHPS-1, and integrin associated protein (IAP) as a complex, the association of IAP with SHPS-1, SHPS-1 phosphorylation and Shc recruitment to SHPS-1, Shc phosphorylation, stimulation of DNA synthesis and cell replication or cell migration. Ligands that bind to β3 through the cysteine loop domain often induce both conformational changes and β3 phosphorylation. Similarly, stimulation of β3 phosphorylation can induce a conformational change in β3 secondarily. β3 phosphorylation is measured by applying the compound that binds to β3 to smooth muscle and endothelial cells in culture. First compounds are added using concentrations varying from 0.1 to 1 µg/ml to confluent smooth muscle or endothelial cell monolayers in 10 cm dishes. Following a fixed time period of exposure to the cells (2-4 hrs) the cells are lysed in 900 µl of RIPA buffer (1,2). The lysates are either analyzed directly by immunoblotting for β3 to measure polymerization or immunoprecipitated with an anti β3 antibody and then immunoblotted for phosphotyrosine. Immunoblotting is analyzed following separation of the proteins contained in 30 µl of cell lysate by SDS polyacrylamide gel electrophoresis (SDS-PAGE). For immunoprecipitation the primary β3 antibody is added at a 1:300 dilution to 900 µl of lysate and incubated overnight. The immune complexes are precipitated with protein A sepharose and eluted with Laemmli sample buffer (Maile L A and Clemmons D R, *Endocrinology* 143: 4259-4264 (2002); Maile L A, Clarke J B, Clemmons D R, *J Biol Chem*, 277:8955-8960 (2002)). The amount of phosphorylated β3 is then determined by SDS-PAGE followed by immunoblotting with a monoclonal anti-phosphotyrosine antibody (PY99) (Ling Y, Maile L A, Clemmons D R, *Mol Endocrinol*, 17:1824-1833 (2003)).

The methodology for determining complex formation between SHPS-1 and IAP has been previously published (Maile L A, Clarke J B, Clemmons D R, *Mol Biol Cell*, 14:3519-28 (2003)). Briefly the cells are exposed to test agents that activate β3 through the cysteine loop domain and then they are exposed to IGF-I. Following IGF-I exposure if β3 is ligand occupied by an activating ligand IAP and SHPS-1 will associate in a large molecular weight complex. Importantly if this is completely inhibited by antibody that binds to the cysteine loop domain or other inhibitors, they will not associate. To detect this complex cell lysates are prepared as described previously and immunoprecipitated for SHPS-1 using a 1:330 dilution of a polyclonal antiserum. The immunoprecipitated proteins are separated by SDS-PAGE and immunoblotted using a purified monoclonal antibody to detect IAP (B6H12) (Id.).

SHPS-1 Phosphorylation. To determine SHPS-1 phosphorylation the β3 ligand (either agonist or antagonist) is added to the cultures for periods between 30 minutes and 2 hrs at 37° C. IGF-I is then added and cell lysates are prepared at specific time points. In addition to baseline 3, 5, 10, and 20 min lysates are prepared after exposure to IGF-I. The lysates are prepared as described previously and immunoprecipitated for SHPS-1 using anti-SHPS-1 polyclonal antiserum at a 1:330 dilution. The immunoprecipitate which is pelleted with protein A sepharose is then analyzed by SDS-PAGE followed by immunoblotting for phosphotyrosine using the PY99 monoclonal antibody that detects phosphorylated tyrosine residues (Maile L A and Clemmons D R, *Endocrinology* 143: 4259-4264 (2002); Maile L A, Clarke J B, Clemmons D R, *J Biol Chem*, 277:8955-8960 (2002); Maile L A and Clemmons D R *Circ Res*, 93: 925-931 (2003)). The expected response is that IGF-I stimulates SHPS-1 phosphorylation and that agonists will increase either the intensity of SHPS-1 phosphorylation or prolong its duration. In contrast, antagonists will decrease the intensity and shorten its duration.

Shc Phosphorylation. The binding and recruitment of Shc to SHPS-1 is critical for Shc phosphorylation which is necessary for IGF-I signaling particularly in smooth muscle cells and endothelium in diabetes. To measure Shc phosphorylation cell cultures are exposed to agonists or antagonists as described previously and then cell cultures are then exposed to IGF-I for periods of 10, 20 or 30 minutes. Cell lysates are prepared at each time point as described previously and immunoprecipitated using a 1:1000 dilution of anti-Shc polyclonal antiserum. The immunoprecipitate is cleared with protein A sepharose and then the proteins eluted with Laemmli sample buffer and analyzed by SDS-PAGE followed by immunoblotting with the anti phosphotyrosine antibody PY99. The expected response is that IGF-I will stimulate Shc Phosphorylation. This will be significantly prolonged and intensified particularly at the later time points in cultures exposed to β3 agonists. In contrast, antagonists will inhibit Shc phosphorylation.

Shc Recruitment to SHPS-1. Cultures are exposed to either agonists or antagonists for the time periods listed previously. Cultures are then washed and IGF-I is added for periods of 5, 10, 20 or 30 min. Cell lysates are prepared as described previously (Maile L A and Clemmons D R, *Endocrinology* 143: 4259-4264 (2002)) and immunoprecipitated using anti-SHPS-1 antisera using a 1:330 dilution. Following clearing of the immune complexes with protein A sepharose, the immunoprecipitates are analyzed by SDS-PAGE followed by immunoblotting for Shc using a 1:2000 dilution of anti-She antiserum. The expected response is that IGF-I will stimulate Shc recruitment to SHPS-1 which is required for Shc to undergo phosphorylation. However if an antagonist is used, then SHPS-1 will not be phosphorylated and Shc will not bind to SHPS-1 therefore recruitment will be undetectable or greatly diminished.

Activation of MAP kinase. Activation of MAP kinase is critical for stimulation of cell division and cell migration in smooth muscle cells and endothelium by IGF-I. Shc phosphorylation and recruitment to the membrane as noted previously is required for MAP kinase activation. To determine if MAP kinase activation is impaired, cells are exposed to agonists or antagonists for the periods of time described previously then cell lysates prepared as described previously (Maile L A and Clemmons D R *Circ Res*, 93: 925-931 (2003)). 30 µl of cell lysate is analyzed directly by SDS-PAGE with immunoblotting for the phosphorylated form of ERK 1/2 (an indication of MAP kinase activity) (Ling Y, Maile L A, Clemmons D R, *Mol Endocrinol*, 17:1824-1833 (2003)). It would be anticipated that the time course intensity of MAP kinase activation will be prolonged by β3 agonists and inhibited by β3 agonists.

Cell Replication. Smooth muscle and/or endothelium are plated at relatively low density, $10^4/cm^2$ in low serum (0.2%) containing medium. 24 hr after plating, cells are quiesced in 0.2% platelet poor plasma containing medium. 24 hr later the cultures are exposed to increasing concentrations of IGF-I between 0 and 100 ng/ml and the β3 agonists or antagonists. After 48 hr, the cell cultures are stained with trypan blue and the cell number is determined by manual counting. If β3 is occupied by an agonist then there is at least a 2 fold increase in cell number over this time period. Whereas if an antagonist is added there is often less than 20% increase in cell number.

Cell Migration. Confluent quiescent smooth muscle or endothelial cell cultures are wounded with a razor blade as described in Maile L A, Imai Y, Clarke J B, Clemmons D R, *J. Biol. Chem.*, 277:1800-1805 (2002). The wounds are examined to determine that a straight edge has been obtained and there are no grooves in the plate. At least five areas that are correctly wounded are then identified with a color marker. IGF-I is added at concentrations of either 50 or 100 ng/ml and various concentrations of the angonists or antagonists are added to at least duplicate cultures. After 72 hr the number of cells that have migrated at least 50 microns from the wound edge are determined and counted following staining with methylene blue. IGF-I normally stimulates between 20 and 50 cells per microscopic field to migrate this distance. In the presence of an antagonist, there is generally fewer than 5 cells/microscopic field that migrate but agonists may increase the response to IGF-I by as much as 2 fold.

The present invention is explained in greater detail in the following non-limiting Examples.

EXAMPLE 1

DNA Synthesis

Cells are plated at a density of $2.5 \times 10^4/cm^2$ in 96-well tissue culture plates and grown for 5 days without a medium change. They were rinsed once with serum-free DMEM and serum starved by incubating with DMEM plus 0.2% platelet poor plasma (PPP) for 24 h. The cells are then exposed to IGF-I plus any treatment and incubated at 37 C for 24 h, and the amount of [$^3$H]thymidine incorporated into DNA was determined as described in: Imai Y and Clemmons D R. Roles of Phosphatidylinositol 3-Kinase and Mitogen-Activated Protein Kinase Pathways in Stimulation of Vascular Smooth Muscle Cell Migration and Deoxyriboncleic Acid Synthesis by Insulin-Like Growth Factor-I. *Endocrinology* 140, 4228-4235 (1999).

EXAMPLE 2

Peptide Synthesis

Peptides are synthesized using FMOC chemistry on a Rainin Multiple Peptide synthesizer. Activation of FMOC amino acids and acylation utilizes HATU in the presence of a base (N methyl morpholine). Upon completion of acylation, the FMOC protecting group is removed with 20% piperidine in dimethylformamide. After synthesis, the peptide is removed from the resin and deprotected by treatment with 95% trifluoroacetic acid containing appropriate organic scavengers.

Cleaved, deprotected peptides are precipitated in cold ether, resuspended in a dilute TFA/acetonitrile mix, and purified by high performance liquid chromatography on a reverse phase resin with an increasing acetonitrile gradient.

Quality control of the peptide product is assessed by analytical HPLC and by matrix assisted laser desorption ionization time-of-flight mass spectrometry. Purified peptide is lyophilized and stored at −20° C.

EXAMPLE 3

Identification of Agonists

As noted above, the agonists bind to a specific region on the αVβ3 integrin receptor that has not been identified previously as a region that would result in receptor activation. All agonists that we have determined to bind in this region contain a region of sequence that is commonly termed a heparin binding domain. This heparin binding domain is present in 5 ligands that we have found to date that bind to this region of αVβ3. The documentation that they bind to a specific region of αVβ3 has been provided by two types of experiments. First we have a polyclonal antibody that is known to react with this region of αVβ3, which is the region of the β3 subunit that is located between amino acids at positions 177 and 183. When this polyclonal antibody is incubated with any of the known agonists, it completely inhibits their ability to bind.

A more definitive experiment was conducted in which the identical region of the β1 integrin was substituted by mutagenesis for this 8 amino acid region within β3. The mutant protein was then expressed in CHO cells which do not constitutively express β3. Binding assays were then conducted using these ligands. It was shown that this mutation resulted in a complete loss of binding and an inability to activate β3. Activation was measured by β3 phosphorylation which has been shown to be stimulated by binding of these agonists to this region of β3. These data indicate this is the region of β3 that binds to these ligands.

EXAMPLE 4

Identification of Antagonist

A synthetic peptide bearing the following structure: KKQRFRHL (SEQ ID NO: 6) was found to have inhibitory activity in each of these biologic assays. Activation of the IGF-I receptor by IGF-I could be inhibited by approximately 60%. Furthermore analysis has shown that a cyclized peptide containing this sequence is a more potent inhibitor. Substitution of a hydrophobic residue for arginine at position 208 results in the greatest loss of activity.

EXAMPLE 5

Additional Agonists

Additional peptide agonists that can be used to carry out the present invention are set forth in Table 1 below. Such peptide agonists are synthesized as described in Example 1 above.

TABLE 1

Examples of additional IGF-I agonist peptides.

Agonist ($X_m$BBXXABBBX$_n$)* (SEQ ID NO: 7)

KKQRFRHR (SEQ ID NO: 8)

RKQRFRHR (SEQ ID NO: 9)

KRQRFRHR (SEQ ID NO: 10)

TABLE 1-continued

Examples of additional IGF-I agonist peptides.

KKQRFKHR (SEQ ID NO: 11)

KKQRFRHK (SEQ ID NO: 12)

KKQRFRRR (SEQ ID NO: 13)

KKQRFRKR (SEQ ID NO: 14)

KKQRFRHR (SEQ ID NO: 15)

HKQRFRHR (SEQ ID NO: 16)

KHQRFRHR (SEQ ID NO: 17)

RRQRFRHR (SEQ ID NO: 18)

KKQFKHK (SEQ ID NO: 19)

KKQKFRHR (SEQ ID NO: 20)

KKNRFRHR (SEQ ID NO: 21)

KKQRYRHR (SEQ ID NO: 22)

KKQRWRHR (SEQ ID NO: 23)

KKQRHRHR (SEQ ID NO: 24)

AKKQRFRHRN (SEQ ID NO: 25)

LAKKQRFRHRNR (SEQ ID NO: 26)

SLAKKQRFRHRNRK (SEQ ID NO: 27)

PSLAKKQRFRHRNRKG (SEQ ID NO: 28)

RPSLAKKQRFRHRNRKG (SEQ ID NO: 29)

AKKQRFRHR (SEQ ID NO: 30)

LAKKQRFRHR (SEQ ID NO: 31)

SLAKKQRFRHR (SEQ ID NO: 32)

Agonist (X$_m$BBXXABBBX$_n$)* (SEQ ID NO: 7)

PSLAKKQRFRHR (SEQ ID NO: 33)

RPSLAKKQRFRHR (SEQ ID NO: 34)

KKQRFRHRN (SEQ ID NO: 35)

KKQRFRHRNR (SEQ ID NO: 36)

KKQRFRHRNRK (SEQ ID NO: 37)

KKQRFRHRNRKG (SEQ ID NO: 38)

RPSLAKKQRFRHRN (SEQ ID NO: 39)

RPSLAKKQRFRHRNR (SEQ ID NO: 40)

RPSLAKKQRFRHRNRK (SEQ ID NO: 41)

AKKQRFRHRNRKG (SEQ ID NO: 42)

LAKKQRFRHRNRKG (SEQ ID NO: 43)

SLAKKQRFRHRNRKG (SEQ ID NO: 44)

*B = basic amino acid (R, K, H); X = any amino acid; A = aromatic amino acid (F, Y, W, H).
$m$ = any integer from 0-5, $n$ = any integer from 0-4.

EXAMPLE 6

Additional Antagonists

Additional peptide antagonists that can be used to carry out the present invention are set forth in Table 2 below. Such peptide agonists are synthesized as described in Example 2 above.

TABLE 2

Examples of IGF-I antagonist peptides.

Antagonist (X$_m$BBXXABBHX$_n$)* (SEQ ID NO: 45)

KKQRFRHL (SEQ ID NO: 46)

KKQRFRHA (SEQ ID NO: 47)

RKGRYKRA (SEQ ID NO: 48)

KKQRFRHI (SEQ ID NO: 49)

KKQRFRHV (SEQ ID NO: 50)

KKQRFRHM (SEQ ID NO: 51)

KKQRFRHC (SEQ ID NO: 52)

KKQRFRHF (SEQ ID NO: 53)

KKQRFRHW (SEQ ID NO: 54)

RKQRFRHL (SEQ ID NO: 55)

Antagonist (X$_m$BBXXABBHX$_n$)* (SEQ ID NO: 45)

RKQRFRHI (SEQ ID NO: 56)

RKQRFRHV (SEQ ID NO: 57)

RKQRFRHM (SEQ ID NO: 58)

RKQRFRHC (SEQ ID NO: 59)

RKQRFRHF (SEQ ID NO: 60)

RKQRFRHW (SEQ ID NO: 61)

AKKQRFRHLN (SEQ ID NO: 62)

LAKKQRFRHLNR (SEQ ID NO: 63)

SLAKKQRFRHLNRK (SEQ ID NO: 64)

PSLAKKQRFRHLNRKG (SEQ ID NO: 65)

RPSLAKKQRFRHLNRKG (SEQ ID NO: 66)

AKKQRFRHL (SEQ ID NO: 67)

LAKKQRFRHL (SEQ ID NO: 68)

SLAKKQRFRHL (SEQ ID NO: 69)

PSLAKKQRFRHL (SEQ ID NO: 70)

RPSLAKKQRFRHL (SEQ ID NO: 71)

KKQRFRHLN (SEQ ID NO: 72)

KKQRFRHLNR (SEQ ID NO: 73)

KKQRFRHLNRK (SEQ ID NO: 74)

KKQRFRHLNRKG (SEQ ID NO: 75)

RPSLAKKQRFRHLN (SEQ ID NO: 76)

RPSLAKKQRFRHLNR (SEQ ID NO: 77)

TABLE 2-continued

Examples of IGF-I antagonist peptides.

RPSLAKKQRFRHLNRK (SEQ ID NO: 78)

AKKQRFRHLNRKG (SEQ ID NO: 79)

LAKKQRFRHLNRKG (SEQ ID NO: 80)

SLAKKQRFRHLNRKG (SEQ ID NO: 81)

*B = basic amino acid (R, K, H); X = any amino acid; A = aromatic amino acid (F, Y, W, H) and H = hydrophobic amino acid (I, L, V, M, F, W, C). H (when referring to hydrophobic amino acid and not referring to histidine) may also be phospho-serine (S-PO$_4$).
$m$ = any integer from 0-5, $n$ = any integer from 0-4.

EXAMPLE 7

Preparation of Peptide for Immunization

In order to prepare an antibody, the sequence of the β3 subunit that binds to the heparin binding domain of vitronectin and other ligands, a synthetic peptide was prepared. The peptide was synthesized using FMOC chemistry using a Rainin multiple peptide synthesizer. Activation of FMCO amino acids and acylation utilizes HTAU in the presence of a base (n-methylmorpholine). Upon completion of acylation, the FMOC protecting group is removed with 20% piperidine in dimethylformamide. After synthesis, the peptide is removed from the resin and deprotected by treatment with 95% trifluoroacetic acid containing appropriate organic scavengers. Cleaved and deprotected peptide was then precipitated with cold ether and resuspended in dilute TFA/acetonitrile and purified by high performance liquid chromatography on a reverse phase resin and eluted with an increasing acetonitrile gradient. The quality of the peptide product was assessed by analytical HPLC and by matrix assisted laser desorption ionization time-of-flight mass spectrometry. The purified peptide was then lyophylized and stored at −20 C. The mass of eluting peptide was verified as containing the correct amino acids by comparison to the known masses in the database.

Conjugation of the β3 cysteine loop peptide (CYDMKTTC) (SEQ ID NO: 82) to Imject Maleimide Activated Mariculture Keyhole Limpet Hemocyanin (Pierce, Rockford, Il.). 0.7 mg, 1.2 mg and 2.1 mg amounts of peptide were weighed and each was dissolved separately before addition to KLH in 500 mcl of 0.03 M NaH$_2$PO$_4$, pH 7.2 containing 0.9 M sodium chloride. 2 mg of maleimide activated KLH was dissolved in 500 mcl of distilled water. 0.7 mg of dissolved peptide was then added to the KLH solution and incubated at room temperature for 20 min. An additional tube containing 0.7 mg of peptide dissolved in buffer and added to the same KLH solution was incubated again 25 min at room temperature. 1.2 mg and 2.1 mg of peptide were sequentially added to the KLH solution and further incubated for 1 hr intervals after each addition, at room temperature. The peptide conjugate was removed and dialyzed 24 hr against 21 of 0.083 M sodium H$_2$PO$_4$ pH 7.2, 0.9 M NaCl with one exchange. The total 4.7 mg of peptide/KLH conjugate was divided into 5 equal aliquots, lyophylized and frozen at −20° C. for later use.

EXAMPLE 8

Rabbit Immunization

New Zealand white rabbit females between 2 and 3 months of age were used for immunization. One of the 5 lyophylized aliquots containing 1.34 mg of conjugate was dissolved in 450 mcl of distilled water. 450 mcl of complete Freunds adjuvant was added and the mixture homogenized. 10 intradermal injections containing between 40-50 ul of mixture per injection were utilized and injected into the rabbits back. After an interval between 4 and 5 weeks the animal was bled and 9-11 ml of whole blood was removed. The animal then received a booster injection containing 1.3 mg of conjugate dissolved in 450 mcl of distilled water containing 450 ul of incomplete Freunds adjuvant. This mixture was injected at one site subcutaneously. The rabbit was then bled monthly via the central ear artery, collecting 9-12 ml at each bleed. The immunizations were repeated 4 times and bleeding conducted at 4-5 week intervals.

EXAMPLE 9

Antibody Purification

The antibody was purified over a protein G affinity column that had been purchased from Sigma. 10-15 ml of crude rabbit serum was diluted with an equal volume of 25 mM sodium H$_2$PO$_4$, pH 7.2 and passed multiple times over a protein G affinity column previously equilibrated in the same buffer for 16 hrs at 4° C. The column was then eluted with 10 column volumes (100 ml total) of 25 mM sodium phosphate 7.2 and the IgG eluted with 0.1 M glycine HCL, pH 2.7. The chromatographic fractions containing the antibody were neutralized with 1.0 M TRIS, pH 9 to pH 7.2 and dialyzed against 25 mM sodium phosphate, ph 7.2 containing 50 mM sodium chloride. After dialysis the protein G purified antibody was stored −20° C.

EXAMPLE 10

Preparation of Affinity Column and Antibody Purification

In order to purify the antibody from whole serum, a peptide affinity column was prepared that contained the exact amino acid sequence of immunogen. The cysteine loop peptide (CYDMKTTC) (SEQ ID NO: 82) was coupled to agarose using Sulfolink coupling gel (Pierce Chemical Co.). 5 ml of coupling gel was equilibrated with a buffer containing 50 mM Tris pH 8.5, 5 mM sodium ETDA. 0.7 mg of the synthetic peptide was dissolved in 1 ml of coupling buffer and added to 5 ml of gel and incubated at room temperature with mixing for 30 min. The procedure was repeated with 0.8 and 2 mg aliquots of peptide added sequentially to the same tube containing the coupling gel and incubated for 30 min. During the last step 3.2 mg of peptide in the coupling buffer was added and the whole mixture reincubated for an additional 3 hr. After the final 3 hr incubation, the material was spun at 1000×g and the supernatant removed. 5 ml of 50 M cysteine in the above described buffer was added to the coupling gel and the incubation continued at room temperature for 1 hr with gentle mixing to block unreacted sites. The gel was stored in 0.25% sodium azide in distilled water until use. To purify the antibody the affinity column was first equilibrated with 50 mM Tris pH 7.2 containing, 50 mM sodium chloride. The antibody pool that had been eluted from the protein G affinity column and previously dialyzed was circulated over the column for 36 hr. The column was washed with 10 column volumes (100 ml) of the loading buffer and eluted with 0.1 M glycine, pH 2.7. The antibody was then neutralized with 1 M Tris, pH 9 and stored at −20° C. until use. The final protein concentration was 180 mcg/ml.

EXAMPLE 11

Production and Screening of Monoclonal Antibodies

Immunization. Pathogen-free Swiss Webster mice are utilized for immunization. The conjugated peptide described above is mixed with emulsified mouse RIBI (MPL+TDD™ emulsion) adjuvant and 300 mcg of the emulsified antigen injected intraperitoneally. The injections are repeated at three week intervals, twice. Antibody titers are determined by withdrawing 50-100 mcl of blood from the tail vein at these three week intervals. The titer is determined by testing the reactivity of the mouse serum for immobilized β3 antigen. In mice where sufficient antibody titer is obtained after six weeks the mice are sacrificed and the spleens and lymph nodes removed for fusion to myeloma cells for hybridoma formation.

Hybridoma Formation. Two mice are selected for spleen harvest. These mice are boosted a third time with 300 mcg of antigen then four days later sacrificed.

Blood and spleen are collected. Spleen cells will be harvested and fused with 63-AGA.65 (ATCCCRL-1580) cells using a 50% PEG solution. These fused cells are then plated in a 96 well plate at $1 \times 10^5$ cells per well in HAT selection medium. After 12-14 days the fusion plates or clones are fed in HT media. At this time medium is collected for screening by ELIZA assay as described below to identify desired hybridoma cells.

ELISA Materials. The ELISA is carried out with the following materials:

96 well Immulon IV plates (Fisher Cat #14-245-153)
1×coating buffer (0.05M carbonate/bicarbonate buffer pH 9.6 Sigma
Cat # C3041)
2% BSA in PBS (Blocking Buffer)
0.5% BSA in PBS (ELISA Buffer)
0.05% Tween PBS (Wash buffer)
DEA developer The DEA Developer (for 500 ml): is produced from 4.8 ml of 85% Diethanolamine (Fisher Cat # D45); 0.25 ml of 1M $MgCl_2$; and pNPP tablets (Sigma Cat # N2765). To prepare the developer, dissolve DEA in 400 ml of sterile water and adjust pH to 10 with HCL and NaOH. Add $MgCl_2$. Bring volume up to 500 ml. Store at 4° C. Wrap in foil to protect from light. Immediately before use add 1 tablet of pNPP to 20 ml of buffer The Secondary Antibody is goat anti mouse IgG alkaline phosphatase conjugate (Jackson Immunoresearch Cat #115-055-164)

Peptide at 1 mg/ml in PBS.

ELISA Method. With materials prepared as described above, ELISA screening of monoclonal antibodies produced as described above is carried out to isolate and provide a monoclonal antibody of the present invention as follows:

1. Coat plates with 50 μl/well of peptide in coating buffer at concentration of 5 μg/ml at 4° C. overnight.
2. Wash plates with 0.05% Tween
3. Block plates with 200 μl/well blocking buffer overnight at 4° C.
4. Repeat step 2
5. Add primary antibody (test antibody) at 40 μl/well (Supernatants) or 50 μl/well (serum dilutions) and incubate for 1 hour at room temperature
6. Wash plates with 0.05% Tween in PBS
7. Add 50 μl/well of secondary antibody at 1:2000 dilution and incubate at room temperature for 1 hour
8. Wash plates with 0.05% Tween in PBS
9. Add 50 μl/well of DEA developer and allow to incubate
10. Read in spectrophotometer at 405 nM.

Hybridoma LAM-CLOOP 101, which produces an antibody of the present invention, was produced by the methods described above.

The foregoing is illustrative of the present invention, and is not to be construed as limiting thereof. The invention is defined by the following claims, with equivalents of the claims to be included therein.

---

That which is claimed is:

1. A method of inhibiting IGF-1 actions in a subject in need of treatment for retinopathy, comprising administering to the subject an effective amount of an antibody that: (a) specifically binds to the cysteine loop domain at amino acids 177 to 184 of a human $\beta_3$ integrin, wherein said amino acids consist of SEQ ID NO:82; (b) does not specifically bind to the RGD binding site of a human $\beta_3$ integrin or utilize the RGD binding site of human $\beta_3$ integrin; and (c) specifically binds to the cysteine loop domain at amino acids 177 to 184 of a pig $\beta_3$ integrin, wherein said amino acids consist of SEQ ID NO:82, thereby inhibiting IGF-1 actions in the subject and treating the retinopathy in the subject.

2. The method of claim 1, wherein the antibody is coupled to a detectable group.

3. The method of claim 1, wherein the antibody is coupled to a therapeutic group.

4. The method of claim 1, wherein the antibody is a monoclonal antibody.

5. The method of claim 1, wherein the antibody does not specifically inhibit ligand occupancy of the RGD binding site of the $\beta_3$ integrin.

6. The method of claim 1, wherein the antibody does not stimulate the specific biochemical events that are stimulated by peptides that bind to the RGD domain binding site of human $\beta_3$ integrin.

7. The method of claim 1, wherein the subject is in need of treatment for diabetic retinopathy.

* * * * *